United States Patent
Moskowitz et al.

(10) Patent No.: US 9,801,728 B2
(45) Date of Patent: Oct. 31, 2017

(54) TOOLS FOR IMPLANTATION AND EXTRACTION OF ARTIFICIAL DISCS

(75) Inventors: Nathan Moskowitz, Rockville, MD (US); Mosheh T. Moskowitz, Rockville, MD (US)

(73) Assignee: Nathan C. Moskowitz, Rockville, MD (US)

( * ) Notice: Subject to any disclaimer, the term of this patent is extended or adjusted under 35 U.S.C. 154(b) by 323 days.

(21) Appl. No.: 13/596,038

(22) Filed: Aug. 27, 2012

(65) Prior Publication Data

US 2013/0173002 A1    Jul. 4, 2013

Related U.S. Application Data

(63) Continuation of application No. 11/684,787, filed on Mar. 12, 2007, now Pat. No. 8,251,891, which is a (Continued)

(51) Int. Cl.
*A61B 1/00* (2006.01)
*A61F 2/44* (2006.01)
(Continued)

(52) U.S. Cl.
CPC ............ *A61F 2/44* (2013.01); *A61B 1/00016* (2013.01); *A61B 1/00022* (2013.01);
(Continued)

(58) Field of Classification Search
CPC ............ A61B 1/00052; A61B 1/00016; A61B 1/3135; A61B 1/07; A61B 1/0669;
(Continued)

(56) References Cited

U.S. PATENT DOCUMENTS 4,134,044 A * 1/1979 Holmes ..................... 314/209 R
4,234,822 A * 11/1980 Garrison et al. .......... 315/209 R
(Continued)

OTHER PUBLICATIONS

Traynelis, Vincent C., M. D. I Prosthetics and Biologics: The Wave of the Future,,, Clinical Neurosurgery, vol. 50, Proceedings of the Congress of Neurological Surgeons, Philidelphia, PA 2002, Chapter 9, pp. 207-219.
(Continued)

*Primary Examiner* — John P Leubecker
(74) *Attorney, Agent, or Firm* — Fish & Richardson P.C.

(57) ABSTRACT

A hand manipulated endoscopic medical device includes a body having a proximal end, which is hand manipulated, a distal end which includes a manipulator, a light emitting device at the distal end, an imaging device at the distal end. A tool for extracting an artificial lumbar disc from between a pair of vertebral plates includes a handle, a member for transmitting force, and a sharpened end, specially configured to be placed between the artificial disc and the vertebral plate. A tool for implanting or explanting a ball to or from an artificial lumbar disc includes a pinion shaft and a pinion shaft enclosure, with a tightening knob at the proximal end of the shaft enclosure and coupled to the pinion shaft, a pinion at the distal end of the pinion shaft, a grappling device at the pinion, and a pair of semi-circular rings.

19 Claims, 24 Drawing Sheets

Related U.S. Application Data continuation-in-part of application No. 10/964,633, filed on Oct. 15, 2004, now abandoned.

(60) Provisional application No. 60/578,319, filed on Jun. 10, 2004, provisional application No. 60/573,346, filed on May 24, 2004, provisional application No. 60/572,468, filed on May 20, 2004, provisional application No. 60/570,837, filed on May 14, 2004, provisional application No. 60/570,098, filed on May 12, 2004.

(51) Int. Cl.
| | |
|---|---|
| A61B 1/313 | (2006.01) |
| A61B 17/29 | (2006.01) |
| A61F 2/46 | (2006.01) |
| A61B 1/05 | (2006.01) |
| A61B 1/06 | (2006.01) |
| A61B 1/07 | (2006.01) |
| A61F 2/30 | (2006.01) |

(52) U.S. Cl.
CPC ...... *A61B 1/00039* (2013.01); *A61B 1/00048* (2013.01); *A61B 1/00052* (2013.01); *A61B 1/00114* (2013.01); *A61B 1/00117* (2013.01); *A61B 1/05* (2013.01); *A61B 1/0676* (2013.01); *A61B 1/0684* (2013.01); *A61B 1/07* (2013.01); *A61B 1/3135* (2013.01); *A61B 17/29* (2013.01); *A61F 2/4611* (2013.01); *A61B 2017/2932* (2013.01); *A61F 2/442* (2013.01); *A61F 2002/3069* (2013.01); *A61F 2002/30523* (2013.01); *A61F 2002/443* (2013.01); *A61F 2002/4619* (2013.01); *A61F 2002/4627* (2013.01); *A61F 2220/0025* (2013.01)

(58) Field of Classification Search
CPC . A61B 1/00022; A61B 1/00032; A61B 17/29; A61B 2017/2927; A61B 2017/2946
USPC ........................................................ 600/160
See application file for complete search history.

(56) References Cited

U.S. PATENT DOCUMENTS

| | | | |
|---|---|---|---|
| 4,402,311 A * | 9/1983 | Hattori .......................... | 600/117 |
| 4,471,766 A * | 9/1984 | Terayama ..................... | 600/104 |
| 4,554,914 A | 11/1985 | Kapp et al. | |
| 4,636,217 A | 1/1987 | Ogilvie et al. | |
| 4,960,420 A | 10/1990 | Goble et al. | |
| 4,997,432 A | 3/1991 | Keller | |
| 5,123,926 A | 6/1992 | Pisharodi | |
| 5,209,747 A * | 5/1993 | Knoepfler ..................... | 606/16 |
| 5,275,615 A * | 1/1994 | Rose .............................. | 606/208 |
| 5,468,238 A * | 11/1995 | Mersch ........................ | 606/15 |
| 5,514,180 A | 5/1996 | Heggeness et al. | |
| 5,599,350 A * | 2/1997 | Schulze et al. ................ | 606/51 |
| 5,620,458 A | 4/1997 | Green et al. | |
| 5,647,840 A * | 7/1997 | D'Amelio et al. ........... | 600/169 |
| 5,660,188 A | 8/1997 | Groiso | |
| 5,667,472 A | 9/1997 | Finn et al. | |
| 5,746,770 A * | 5/1998 | Zeitels et al. ................. | 606/207 |
| 5,782,832 A | 7/1998 | Larsen et al. | |
| 5,792,165 A * | 8/1998 | Klieman ................ | A61B 17/29 606/170 |
| 5,827,323 A * | 10/1998 | Klieman ................ | A61B 17/29 606/170 |
| 5,873,814 A * | 2/1999 | Adair ............................ | 600/109 |
| 5,928,137 A * | 7/1999 | Green ........................... | 600/160 |
| 5,960,522 A | 10/1999 | Boe | |
| 6,086,528 A * | 7/2000 | Adair ............................ | 600/104 |
| 6,126,689 A | 10/2000 | Brett | |
| 6,315,712 B1 | 11/2001 | Rovegno | |
| 6,368,350 B1 | 4/2002 | Erickson et al. | |
| 6,375,682 B1 | 4/2002 | Fleishmann et al. | |
| 6,416,463 B1 * | 7/2002 | Tsuzuki et al. ............... | 600/130 |
| 6,419,626 B1 * | 7/2002 | Yoon ............................. | 600/109 |
| 6,419,704 B1 | 7/2002 | Ferree | |
| 6,458,159 B1 | 10/2002 | Thalgott | |
| 6,464,633 B1 * | 10/2002 | Hosoda et al. ............... | 600/178 |
| 6,527,804 B1 | 3/2003 | Gauchet et al. | |
| 6,533,818 B1 | 3/2003 | Weber et al. | |
| 6,572,653 B1 | 6/2003 | Simonson | |
| 6,579,318 B2 | 6/2003 | Varga et al. | |
| 6,582,468 B1 | 6/2003 | Gauchet | |
| 6,610,093 B1 | 8/2003 | Pisharodi | |
| 6,641,614 B1 | 11/2003 | Wagner et al. | |
| 6,676,660 B2 * | 1/2004 | Wampler et al. .............. | 606/51 |
| 6,719,794 B2 | 4/2004 | Gerber | |
| 6,723,126 B1 | 4/2004 | Berry | |
| 6,730,088 B2 | 5/2004 | Yeh | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,904,308 B2 | 6/2005 | Frisch et al. | |
| 6,955,671 B2 | 10/2005 | Uchikubo | |
| 7,030,904 B2 | 4/2006 | Adair et al. | |
| 7,037,258 B2 | 5/2006 | Chatenever et al. | |
| 7,097,615 B2 | 8/2006 | Banik et al. | |
| 7,115,144 B2 | 10/2006 | Diaz et al. | |
| 7,118,580 B1 | 10/2006 | Beyersdorff et al. | |
| 7,214,183 B2 * | 5/2007 | Miyake ......................... | 600/131 |
| 7,250,060 B2 | 7/2007 | Trieu | |
| 7,252,633 B2 * | 8/2007 | Obata et al. ................... | 600/118 |
| 7,713,192 B2 * | 5/2010 | Murata .......................... | 600/179 |
| 7,988,215 B2 * | 8/2011 | Seibold .................... | F15B 15/10 254/134.3 FT |
| 2004/0088054 A1 | 5/2004 | Berry | |
| 2004/0177531 A1 | 9/2004 | DiBenedetto et al. | |
| 2004/0204628 A1 * | 10/2004 | Rovegno ....................... | 600/131 |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0085910 A1 | 4/2005 | Sweeney | |
| 2005/0216084 A1 | 9/2005 | Fleischmann | |
| 2005/0273170 A1 | 12/2005 | Navarro et al. | |
| 2005/0273174 A1 | 12/2005 | Gordon et al. | |
| 2005/0278026 A1 | 12/2005 | Gordon et al. | |
| 2006/0004258 A1 * | 1/2006 | Sun et al. ...................... | 600/160 |
| 2006/0020167 A1 | 1/2006 | Sitzmann | |
| 2006/0155168 A1 * | 7/2006 | Pease ............................ | 600/131 |
| 2006/0167340 A1 * | 7/2006 | Pease et al. ................... | 600/127 |
| 2006/0178745 A1 | 8/2006 | Bartish et al. | |
| 2006/0215013 A1 * | 9/2006 | Jongsma et al. ............ | 348/14.08 |
| 2006/0232669 A1 | 10/2006 | Abadie et al. | |
| 2007/0112247 A1 * | 5/2007 | Hirata .......................... | 600/101 |
| 2007/0129604 A1 * | 6/2007 | Hatcher et al. ............... | 600/136 |
| 2007/0185379 A1 * | 8/2007 | Newman et al. .............. | 600/110 |
| 2007/0249904 A1 * | 10/2007 | Amano et al. ................ | 600/131 |
| 2008/0026269 A1 * | 1/2008 | Shurtleff et al. ............... | 429/19 |

OTHER PUBLICATIONS

Wai, E.K. et al., Disk Replacement Arthroplasties: Can the Success of Hip and Knee Replacements be Repeated in the Spine?, Seminars in Spine Surgery, vol. 15, No. 4 Dec. 2003: pp. 473-482.

Richard D. Guyer et al., "Intervertebral Disc Prostheses," Spine Journal, vol. 28, No. 15S, Supp. To Aug. 1, 2003, pp. S15-S23.

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, Dec. 3, 2007, International Application No. PCT/US 07/05005.

* cited by examiner

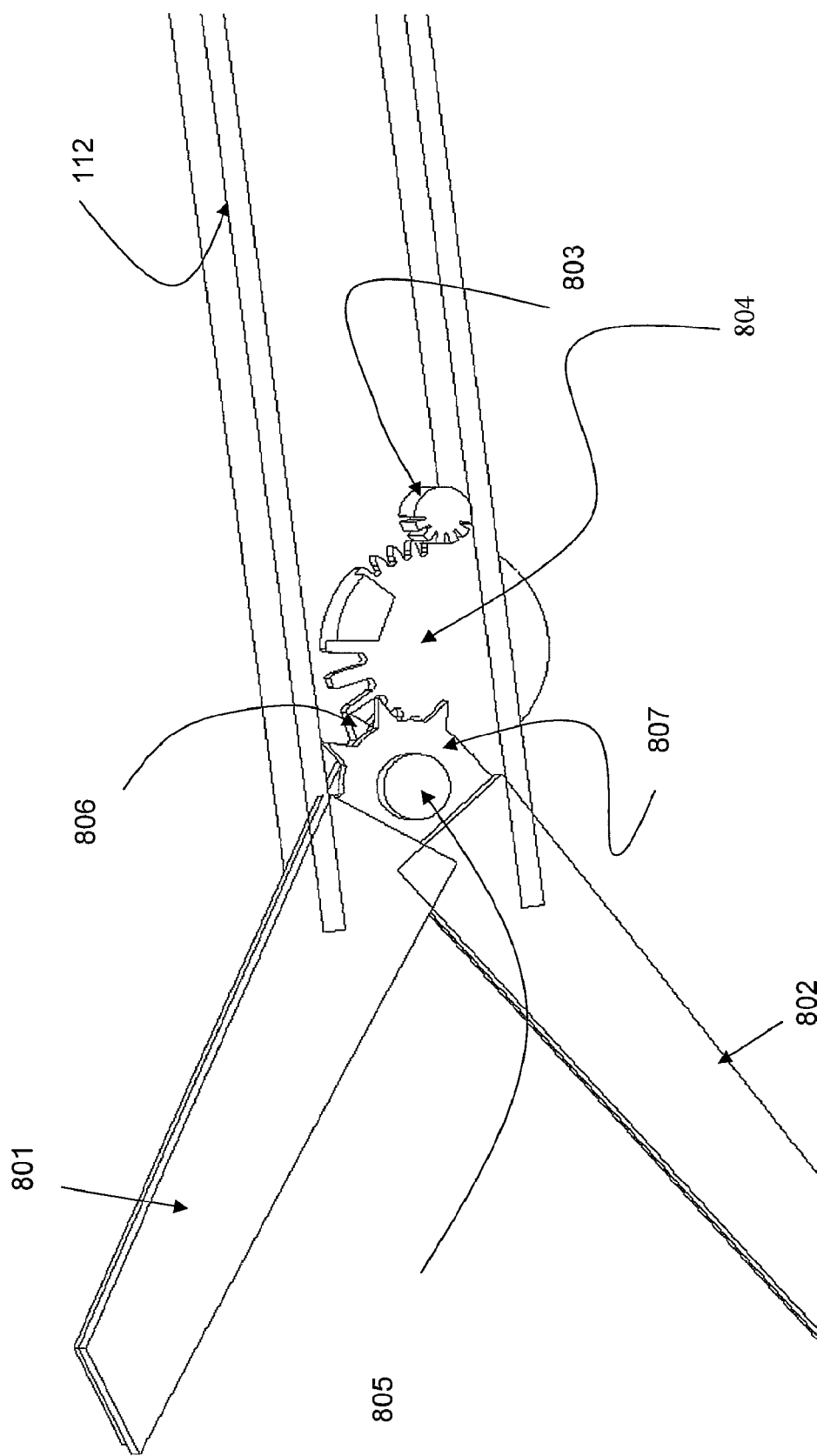

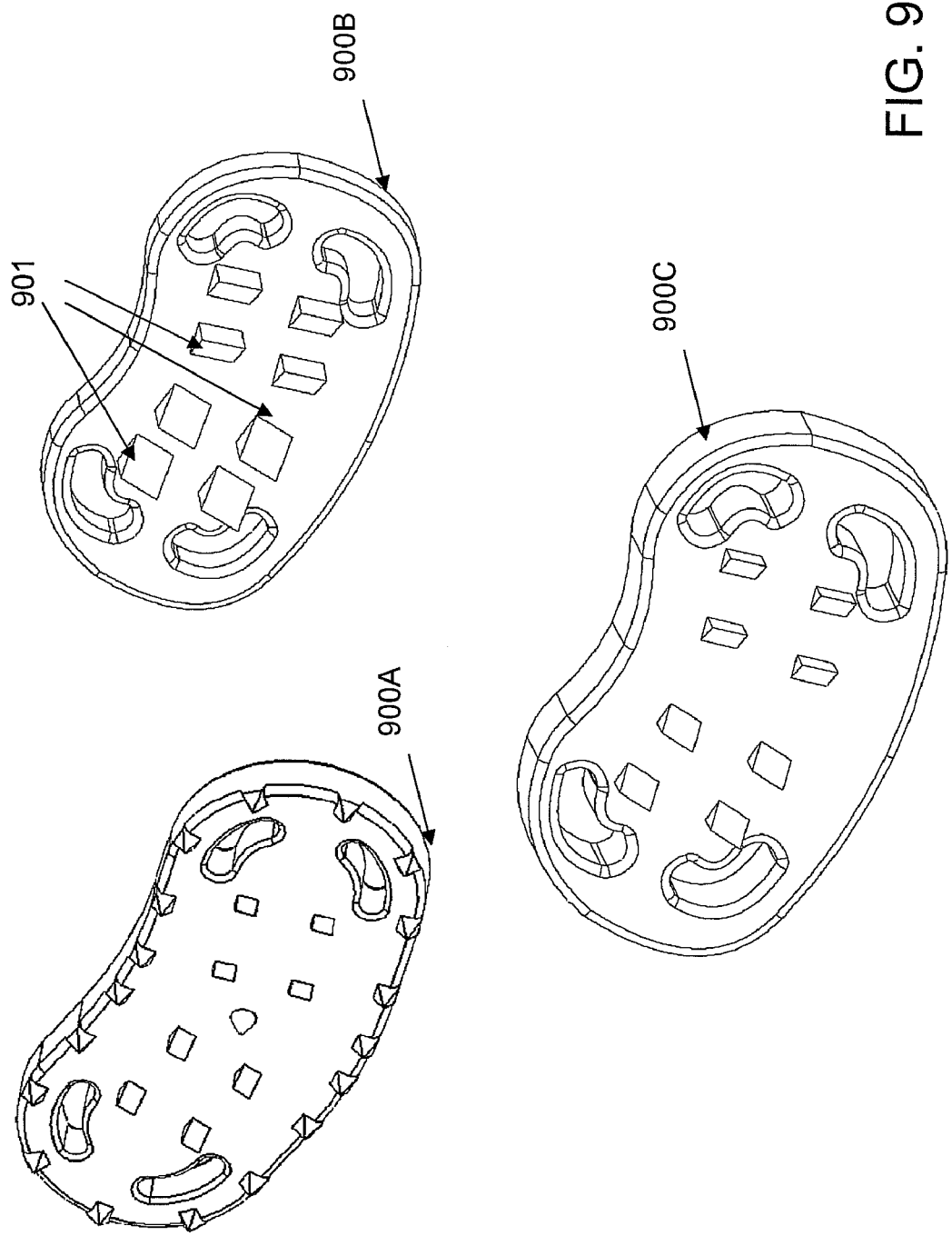

TOOLS FOR IMPLANTATION AND EXTRACTION OF ARTIFICIAL DISCS

The present Application is a Continuation Application of U.S. patent application Ser. No. 11/684,787 filed on Mar. 12, 2007, now U.S. Pat. No. 8,251,891 issued Aug. 28, 2012, which is a Continuation-In-Part Application of U.S. patent application Ser. No. 10/964,633 filed on Oct. 15, 2004, now abandoned, which claims the benefit under 35, U.S.C. §119 (e) of U.S. provisional applications 60/578,319 filed on Jun. 10, 2004; 60/573,346 filed on May 24, 2004; 60/572,468 filed on May 20, 2004; 60/570,837 filed on May 14, 2004; and 60/570,098 filed on May 12, 2004; the entire contents of all the above identified patent applications are hereby incorporated by reference in their entirety.

BACKGROUND OF THE INVENTION

The history of artificial disc placements in the entire human spine, and in particular the lumbar spine has been thoroughly reviewed in Applicants' patent application Ser. No. 10/964,633, filed on Oct. 15, 2004 (abandoned Aug. 10, 2007), patent application Ser. No. 11/487,415, filed Jul. 17, 2006 (now U.S. Pat. No. 7,854,766, issued on Dec. 21, 2010), and in Applicants' issued U.S. Pat. No. 7,083,650. In the '650 patent, Applicants' described the surgical posterior unilateral placement of an artificial lumbar disc. Prior to its surgical placement into a disc space, a complete unilateral discectomy (removal of disc material) must be performed to denude the opposing vertebral body endplates to ensure that the spikes of the artificial disc plates can penetrate the vertebral bodies, and that the disc material is freed from the disc space to allow unencumbered disc motion, and prevention of recurrent disc herniations.

During surgical placement of anterior artificial lumbar discs, visualization of the disc space is not a technical problem because the entire diameter and depth of the disc space can be exposed anteriorly with adequate visualization needed to accomplish surgical disc denudement. This is not as easily accomplished through the unilateral posterior discectomy, where visualization is limited to the side of unilateral implantation, and the middle and contralateral disc can not be visualized completely without causing undue retraction of the lumbar nerve root, and even then, full visualization is not adequately achieved.

To remedy this problem, we disclosed in the '650 patent a wired action-ended pituitary rongeur endoscope with centralized illumination emanating between upper and lower pituitary forceps. The advantage of that design was that it could more easily be placed in the small disc space and provide centralized illumination, neither of which is available in another wired action-ended endoscope design described in U.S. Pat. No. 5,667,472 (Finn et al.), "Surgical instrument and method for use with a viewing system", issued Sep. 16, 1997. In that design the illumination is provided by a tube lateral to the instrument inside the disc space which might endanger the nerve root by over-retraction, and would provide poorer illumination by not focusing on the center of field of vision.

In the present patent application we describe an enhanced design of action-ended endoscopes without encumbrance of wired attachments, and also including a self-contained mounted viewing screen. In totality this design enhances surgical efficiency with respect to operating room time, ergonomics, and financial investment.

To our knowledge, this is the first action-ended endoscope which can function with the complete absence of wires by utilizing a novel induction coil converter converting low voltage power to transient high-powered sparks to initiate gas breakdown of xenon and other molecules, outputting high illumination thereby achieving luminescence equal to wired xenon systems. Another entirely novel aspect of this endoscope is an embodiment which can differentially direct light output in multiple radial and linear directions with digitally controlled reflectors. It can also be easily adapted with lasers to use as a routine laser surgical tool in addition to illumination, forceps grapping, and video display. Furthermore images can be wirelessly transmitted to a mounted self-contained system viewing screen. In addition, it has the capacity to wirelessly transmit images to routine stationary screens, customized work stations, as well as to palm pilots and mobile phones. A further novel application is the ability to manually or electronically control the end manipulator forceps so that it can work as a straight, up or down biter pituitary rongeur combining three types of instruments into one. These modifications with all the above mentioned functions contained within a single action ended-device are entirely unique to endoscopic design to date.

The present invention minimizes operating room clutter associated with routine endoscopic/laser equipment, has a self contained imaging screen, as well as optional therapeutic laser capacities. These functions allow operations to be performed in any sized operating room or military field, thus significantly reducing capital investment, and enhancing surgical and ergonomic efficiency. It also allows surgeries to be performed in places where there might not be any available electrical outlets or electricity or other power sources.

Additional inventions presented here are uniquely related to the design of our lumbar artificial disc design described in application Ser. No. 11/487,415, filed Jul. 17, 2006 (now U.S. Pat. No. 7,854,766, issued on Dec. 21, 2010). These inventions include an instrument which allows easy placement and removal of our lumbar disc ball between upper and lower disc plates, and a disc plate extractor which can extract the device if necessary. There are further modifications of the disc plates including rescue plates with longer spikes, and/or increased plate diameters, akin to rescue screws used for spinal fusion. If a plate falls out under harsh conditions because the spikes are too short, the plate can be rescued with longer/wider spikes or increased width and or ball diameter.

The history of endoscopy, and neuroendoscopy in particular is thoroughly reviewed in "Intracranial endoscopic Neurosurgery", Editor, David F. Jimenez, The American Association of Neurological Surgeons, 1998.

Recent devices to further enhance endoscopic functions include a device which rotates images using an image sensor to act like a gyroscope or a pair of accelerometers, U.S. Pat. No. 7,037,258,B2, (Chatenever et al.) "Image orientation for endoscopic video displays", issued May 2, 2006. A remote surgical support system has been described wherein the state of the surgical instrument and the patient data can be checked in remote control rooms, U.S. Pat. No. 6,955,671 B2, (Uchikubo), "Remote Surgery support system", issued Oct. 18, 2005. Neither of these devices are wireless, or are incorporated into distal action instruments. Neither, do they incorporate any of the advanced technology and wireless transmission of images, or enable differential directional illumination as does our invention.

Another wireless video system entails an in-vivo camera system which is swallowed by the patient, captures and then transmits images of the gastrointestinal tract thereby functioning as an autonomous video endoscope. (See U.S. Pat.

No. 6,904,308 B2 (Frisch et al.), "Array system and method for locating an in vivo signal source", issued Jun. 7, 2005). The patient must wear an antenna array with two antennas. The signals received by the two antennas derive an estimated coordinate set from the signal strength measurements. This innovative device functions specifically as an imaging/camera device. The patient must wear an electrode array to capture the signals over his/her abdomen. It is not designed, nor intended to be a combined surgical tool which performs surgical tool functions e.g. tissue grabbing, suction, cutting etc, which significantly distinguishes it from our invention.

Two more recent patents incorporating wireless technology include U.S. Pat. No. 7,097,615, (Banik et al.), "Robotic endoscope with wireless interface Aug. 29, 2006), and U.S. Pat. No. 7,030,904 B2, (Adair et al.), "Reduced area imaging device incorporated within wireless endoscopic devices" Apr. 18, 2006. Neither of these patents incorporates action-ended instruments or have a self-contained screen imaging system. Furthermore they are purely used for illumination/video, and they do not exploit our innovative technology of an induction coil thermoelectric converter to enhance wireless xenon light. They do not use controlled directional deflectors to modulate light intensity and direction. They do not have laser surgical tool capacities. They are not capable of wireless transmission to palm pilots, or cell phones.

The inventions described herein have great import not only to anterior and posterior spinal endoscopy, but can be modified and used for diagnostic and therapeutic uses in every endoscopic related field including brain, otolaryngological, pulmonary, gastrointestinal, and urological endoscopy, as well as arthroscopic joint surgery including shoulders, hips, knees, ankles, to name but a few. The multifunctional capacities compressed into a single wireless instrument enabling tissue illumination, tissue manipulation, and therapeutic laser directed treatment with a wireless, self-contained mounted viewing screen would also have profound advantages in the fields of military, emergency, ambulatory, and aerospace medicine in areas and situations where sources of electricity are not guaranteed.

BRIEF DESCRIPTION OF THE DRAWINGS

FIG. 8A illustrates a cross-sectional orthonormal view of adjustable, jaw of biter at action end of TWEEAE endoscope (inner fiber light guide absent).

FIG. 9 illustrates a standard lumbar disc plate (A) and rescue plates with larger spikes (B) or thicker plates (C).

DESCRIPTION OF THE PREFERRED EMBODIMENTS

The Medical Device

Figure 1:
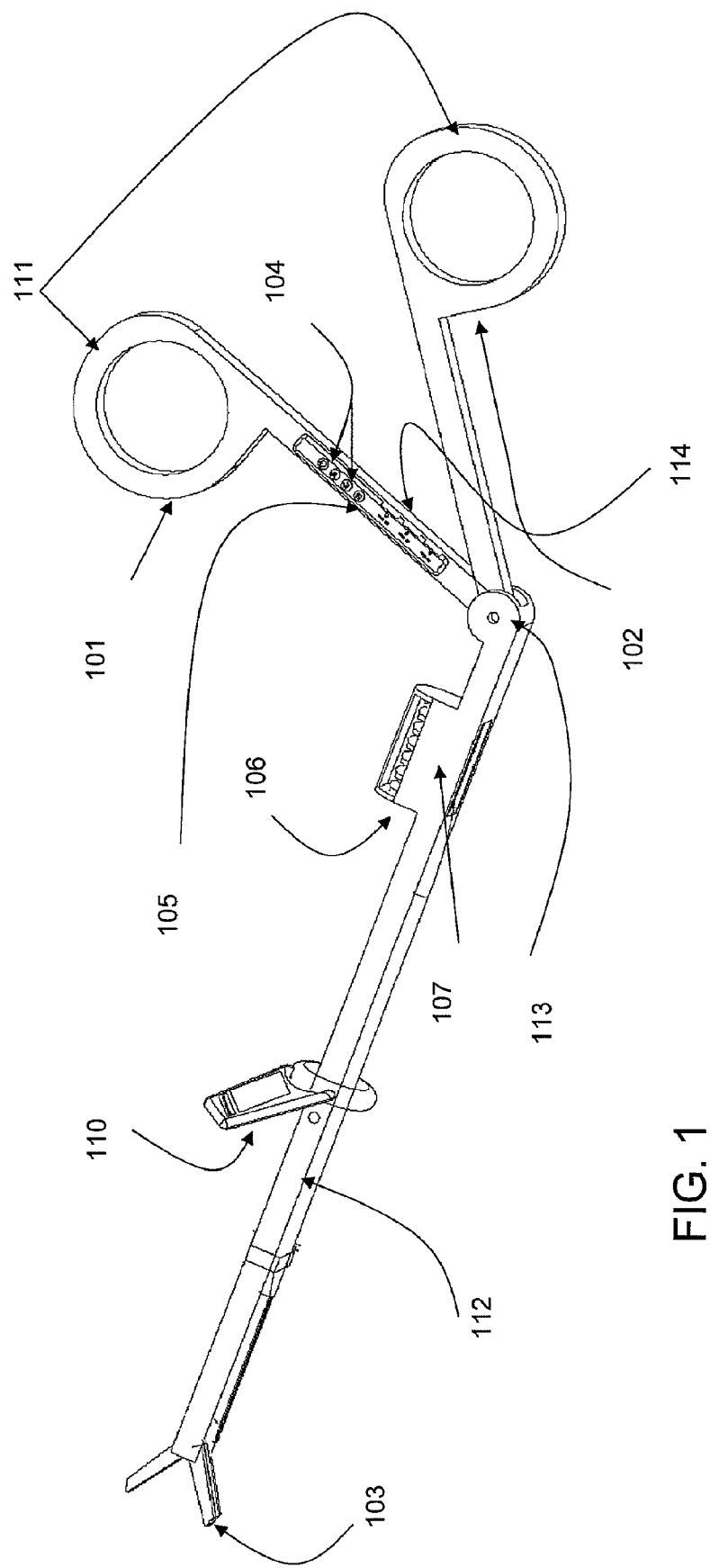
FIG. 1 illustrates a perspective view of the totally wireless electronically embedded action ended (TWEEAE) endoscope.

FIG. 1 illustrates a prospective view of the TWEEAE endoscope having digital inserts 111. This figure demonstrates the medial and distal manipulators 101, 102 which control the opening and closing of the pituitary forceps end manipulator 103. Also illustrated is an on board electronics panel 104 located on the lever 105 of the medial manipulator 101. The electronics panel 104 preferably includes system removable memory 114. Located on the proximal portion of the endoscopic body 112 is the laser and visible light source with cooling apparatus 106 and battery, light, laser compartment 107. Located distal to this component 107 is the mounted system viewing screen 110. The TWEEAE endoscope 100 preferably includes an adjustable manipulator angle of attack 113. We will now describe the electrical and mechanical functioning of the TWEEAE 100.

Figure 2A:
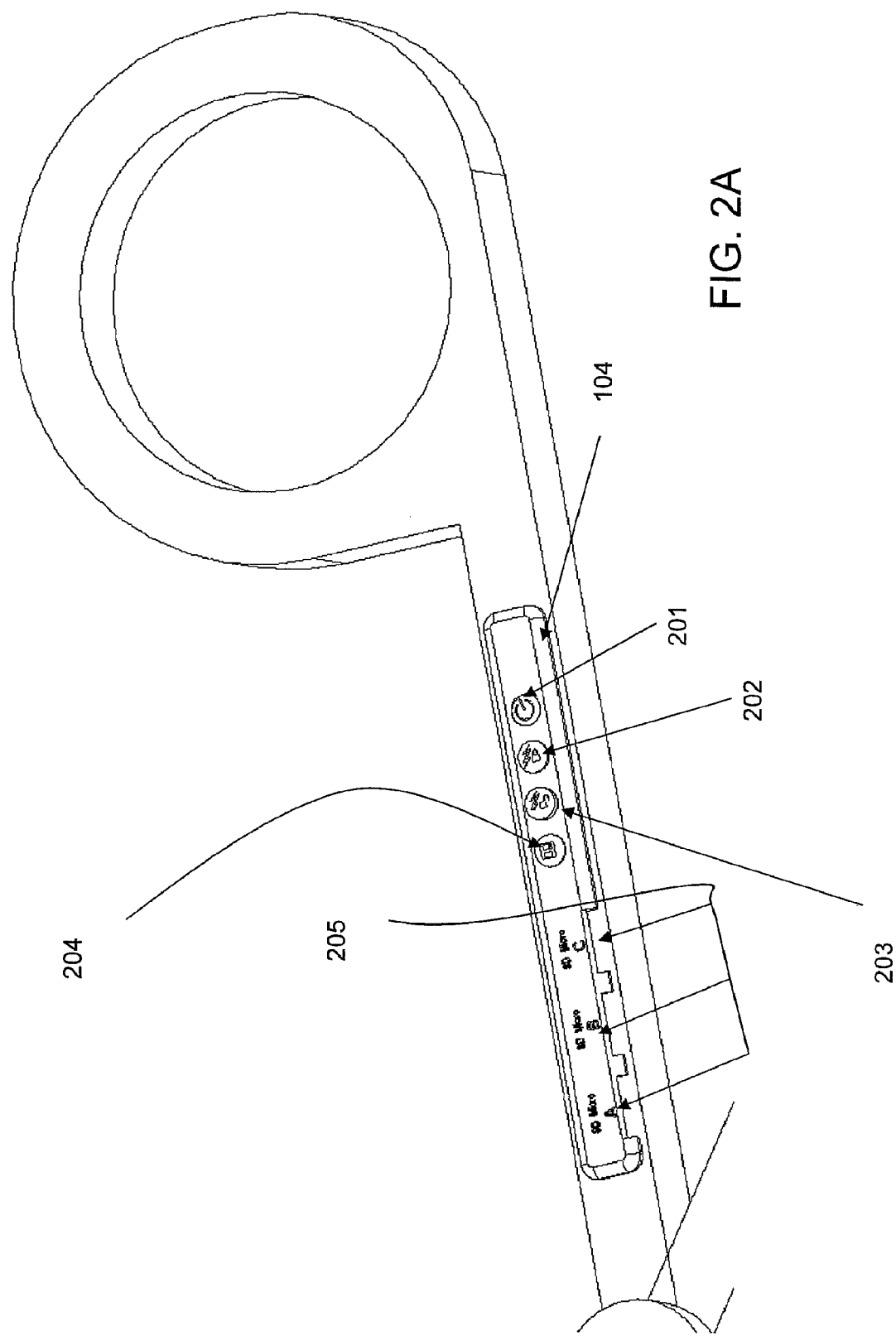
FIG. 2A illustrates an enlarged view of the on board electronics panel located on the medial manipulator lever of the TWEEAE endoscope.

FIG. 2A illustrates an enlargement of the on board electronics panel 114. In order to power up the instrument to initiate usage, the power On-Off button 201, the first button on the right, is depressed once. To turn off or power down, this button 201 is depressed once again.

In order to initiate or terminate wireless transmission of secure video and or data, the second button 202 which is immediately adjacent to the power on/off button 201, with a closed padlock icon is depressed. This information can be transmitted to the mounted system viewing screen 110, to remote unconnected devices such as a mobile phone, palm pilot, personal digital assistant (PDA), or hospital monitors and PCs. This transmission can either be broadcast, and password accessed, in any of the above receivers, or it can be communicated ad-hoc node to node with a remote device.

To transmit non-secure data i.e. open data, the third button 203 with an open padlock icon is depressed. To initiate or terminate saving of video or data into re-removable/re-readable memory drives e.g. micro secure digital the fourth button 204 with a floppy disc icon is depressed. The buttons 201-204 are housed in electronics panel 104. Slots 205 are for removable, rereadable memory drive 114, such as micro-secure digital.

Distal to the four control buttons 201-204 are three slots 205 for inserting and removing micro-secure memory cartridges 114. Slots 205A, B and C are identical slots with the capacity for data storage of contemporary maximum micro-sd capacity. Having three slots 205 multiplies this capacity threefold.

Figure 2B:
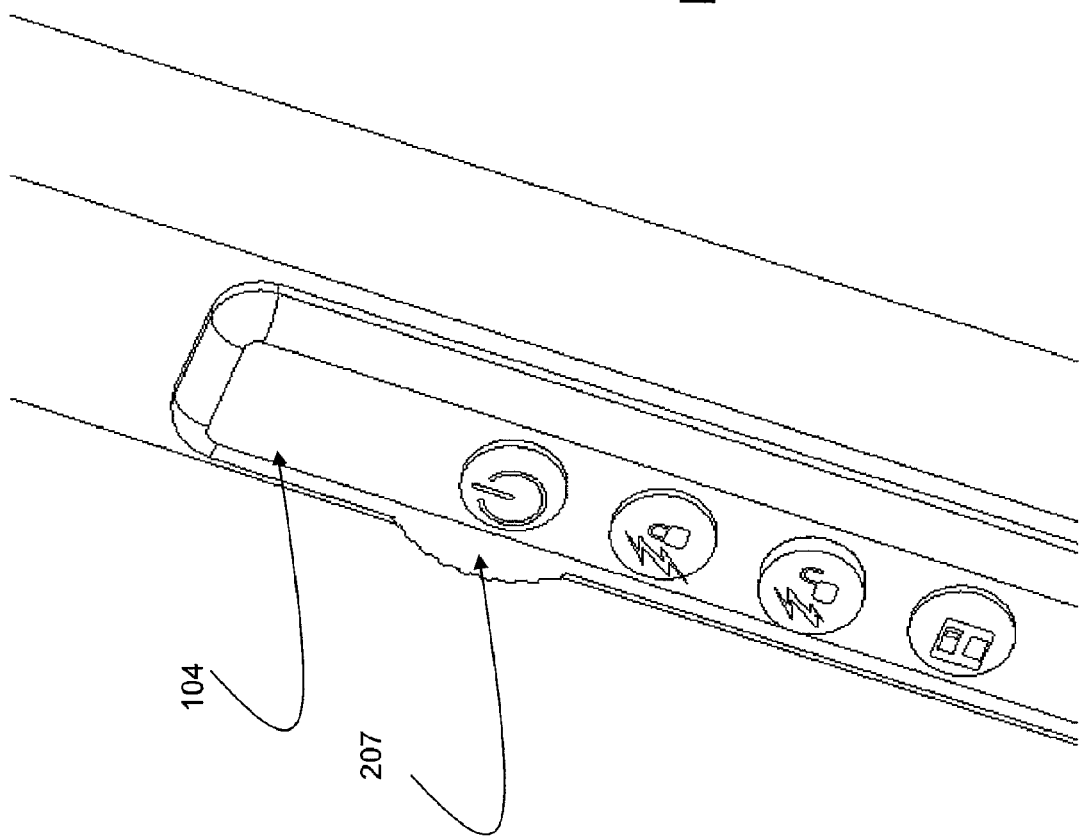
FIG. 2B illustrates the on board electronics panel with optical output dimmer.

FIG. 2B illustrates the on board electronics panel 104 with optical output dimmer 207. Turning the optical output dimming knob 207 will dim or brighten the optical output.

Figure 3A:
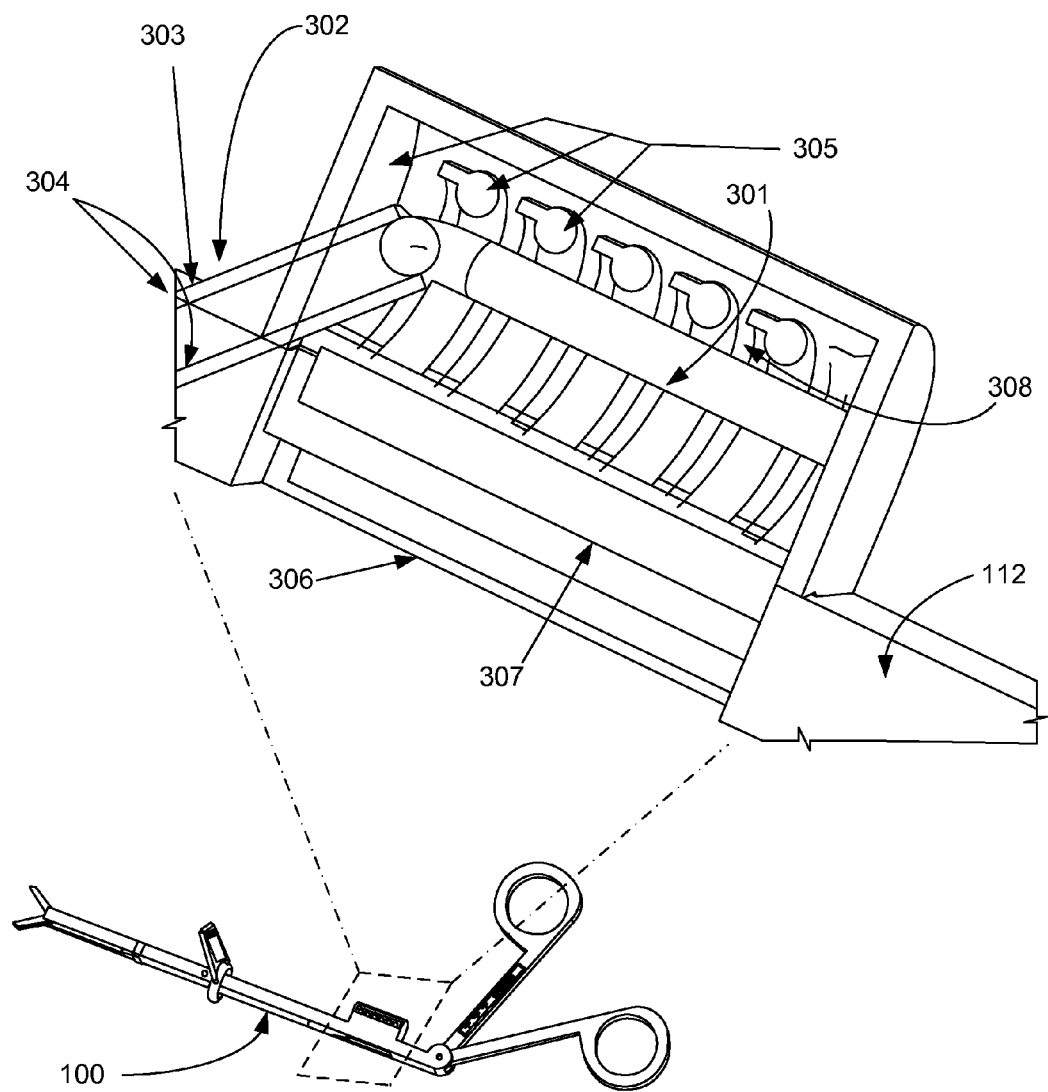
FIG. 3A illustrates a three-dimensional longitudinal section view of the Laser and visible light source with cooling apparatus and battery compartment of the TWEEAE endoscope. Illustrated below is an insert of a miniaturized illustration of the endoscope (100), and the designated localization of the above longitudinal section within the encased relative proximal end of the endoscope.
Figure 3B:
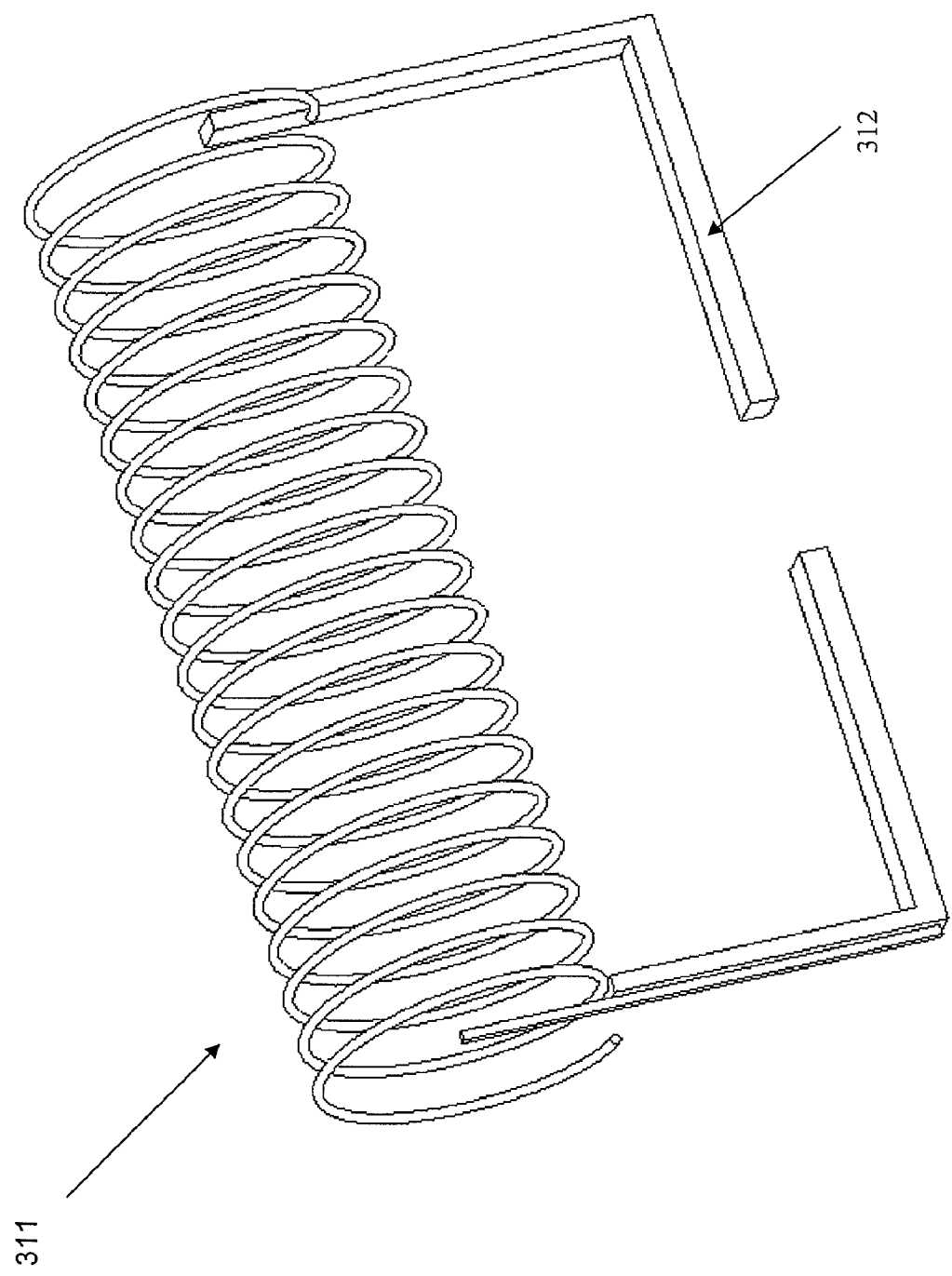
FIG. 3B illustrates the spark (inductor) voltage generator.

FIG. 3A is an enlargement of the laser and visible light source with cooling apparatus 106 and battery compartment 107. Once the power button 201 is depressed this closes a switch between the battery, and both the induction coil within the Magneto and the embedded electronics, on the electronics control panel 104. FIG. 3B illustrates the induction coil 311 (spark voltage generator indicated in FIG. 3A) which generates a high voltage pulse that is used to initiate the ionization of gas molecules inside the gas (xenon) bulb 301 which generates high luminosity white light that is transmitted the fiber optic wave guide. Illustrated in FIG. 3B are the coil 311 and electrodes 312. There may also be a helically wound coolant tube 308, a helical arrangement of thermoelectric conversion units and high efficiency photovoltaic cells 305, a hybrid hydrogen chemical potential cell 306 and an area containing spark (inductor) voltage generator and miniaturized magneto circuitry 307. The fiber optic wave guide 302 may include a core 303 and cladding 304. Alternatively, the gas (xenon) bulb can be a solid state light source. This light then is transmitted through the fiber optic wave guide 302 enclosed in the endoscopic body 112, and is ultimately emanated distally at the end manipulator as optical output.

Alternative embodiments may include a solid state light source i.e. a diode light source as well as a laser source e.g. VCSEL (vertical cavity surface emitting laser), or a quantum cascade laser, a terahertz source, or a yttrium energy source. These embodiments can be used for therapeutic surgical laser treatment of tissues, (not merely illumination) as well as for tissue scanning.

To constantly energize the power battery source FIG. 3 illustrates a helical arrangement of thermoelectric conversion units and high efficiency photovoltaic cells 305 which recaptures heat and light (photonic) energy, respectively which is fed back to a recharge mechanism (not shown). Adjacent to the aforementioned cells 305 is a helically wound coolant tube 308 with liquid flow propelled by a combination of the battery and an electro osmotic unit (not illustrated). A hydrogen cell is ideally suited for this design as it requires constant flow of protons. This cell can be combined with a standard chemical cell for increased power capacity and reliability. This is denoted as a hybrid hydrogen chemical potential cell (Battery) 306.

Figure 4:
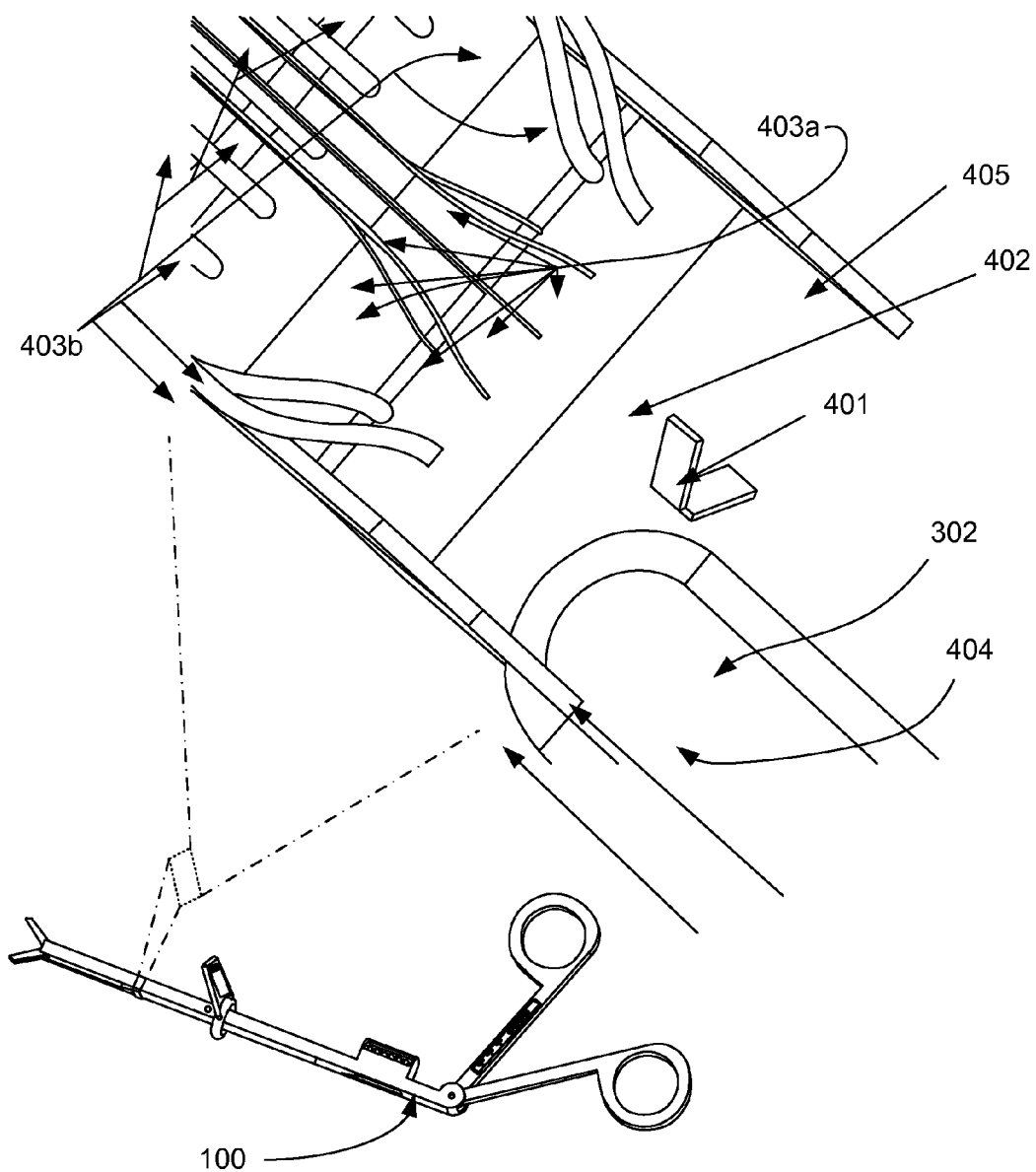
FIG. 4 illustrates a three-dimensional longitudinal sectional view of the spreading pattern for visible and laser light in the more distal body of the TWEEAE endoscope. Illustrated below is an insert of a miniaturized illustration of the endoscope (100), and the designated localization of the above longitudinal section within the encased more distal end of the endoscope.
Figure 5A:
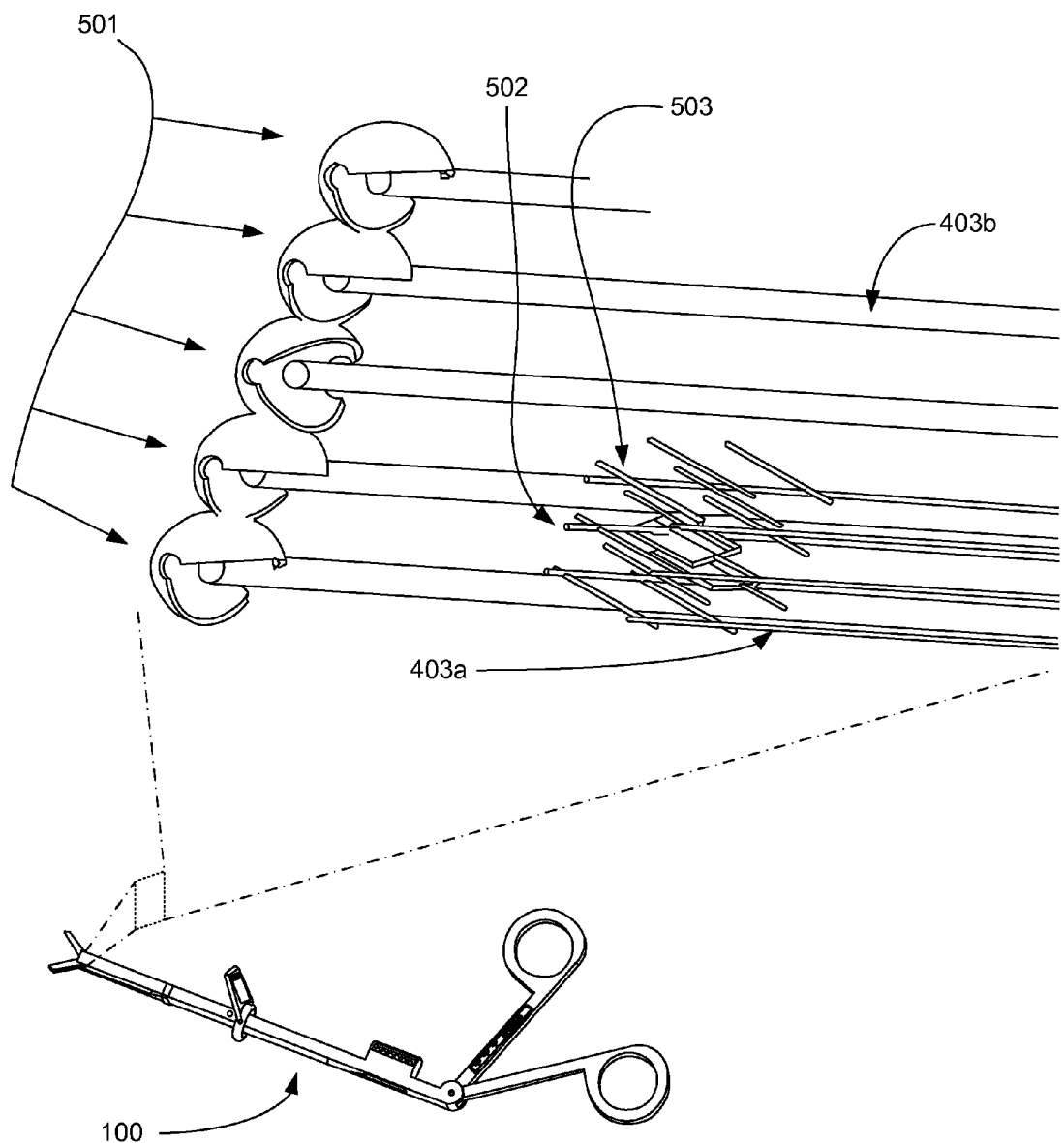
FIG. 5A illustrates a three-dimensional longitudinal sectional view of the fixtures at optical output of the TWEEAE endoscope. Illustrated below is an insert of a miniaturized illustration of the endoscope (100), and the designated localization of the above longitudinal section within the encased distal end of the endoscope.
Figure 5B:
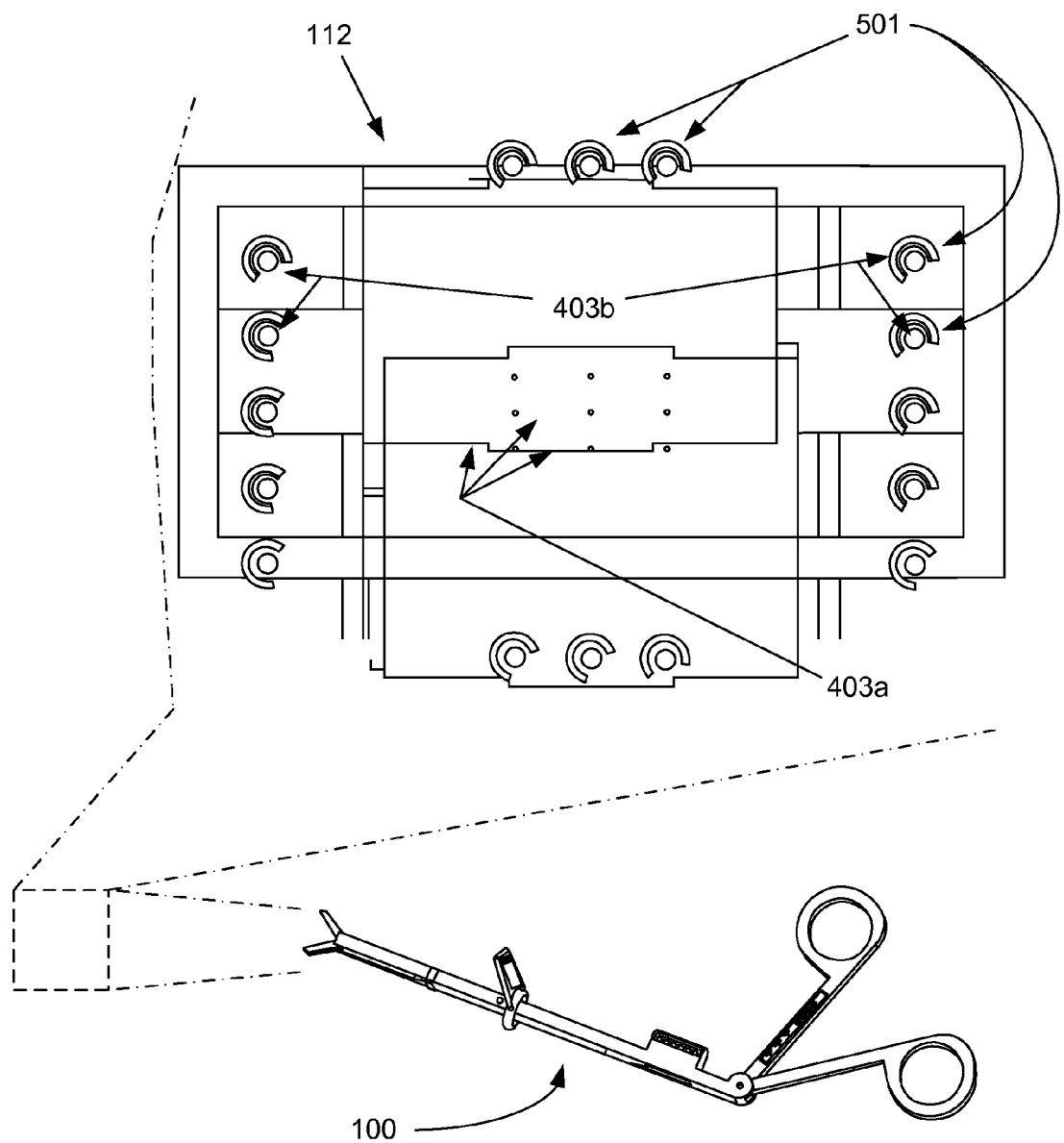
FIG. 5B illustrates a cross-sectional view of guide fibers exiting at action end of the TWEEAE endoscope exhibiting geometric arrangement of beams output. Illustrated below is an insert of a miniaturized illustration of the endoscope (100), and the designated localization of the above cross-sectional view within the encased distal end of the endoscope.

FIGS. 4, and 5A and 5B illustrate the spreading and beam guiding patterns for visible and laser light at the more distal end of the endoscope 100 close to the end manipulator 103. FIG. 4 illustrates the light or laser beam hereafter referred to as the "wave front" 404 entering the beam splitting section 405 which is composed of a three dimensional array of mirrors used to split and redirect the wave front. Illustrated is a beam splitting mirror 401 and a beam directed coated back mirror 402 which directs the wave front to one of twenty-five interior or exterior optical fibers 403*a*, 403*b*. The interior fibers 403*a* preferentially transmit a laser light or radiation, but are also capable of transmitting visible light. The exterior fibers 403*b* preferentially transmit visible light but are capable of transmitting laser light or radiation. Whether or not the laser source or visible light source is transmitted can be programmed or controlled with additional electronics (not illustrated).

FIG. 5A illustrates the path of light distal to that illustrated in FIG. 4. We see the exterior fibers 403*b* which transmit visible light in this depiction. Each of these exterior cables 403*b* terminates within individual elliptical semi-enclosed directive reflectors 501. These reflectors 501 which can be positioned electronically have the ability to form a beam of visible light unto an arbitrary direction.

The Risley prisms or semi-coated mirrors 502 can be used as shown at the terminals of the interior fibers 403*a* to direct a coherent beam of laser light or radiation. Also illustrated are prism or mirror axial inserts 503 that can be electronically rotated to obtain the desired beam direction.

FIG. 5B is an en-face cross sectional image of the guide fibers 403*a*, 403*b* exiting at action end of endoscope exhibiting geometric arrangement of beams output. Illustrated are exterior fibers 403*b* (exaggerated cross sectional thickness) transmitting visible light (preferred) or laser light radiation with their respective surrounding electronically controlled elliptical semi-enclosed directive reflectors. Illustrated centrally are interior fibers 403*a* transmitting laser light or radiation (preferred) or visible light.

Figure 6A:
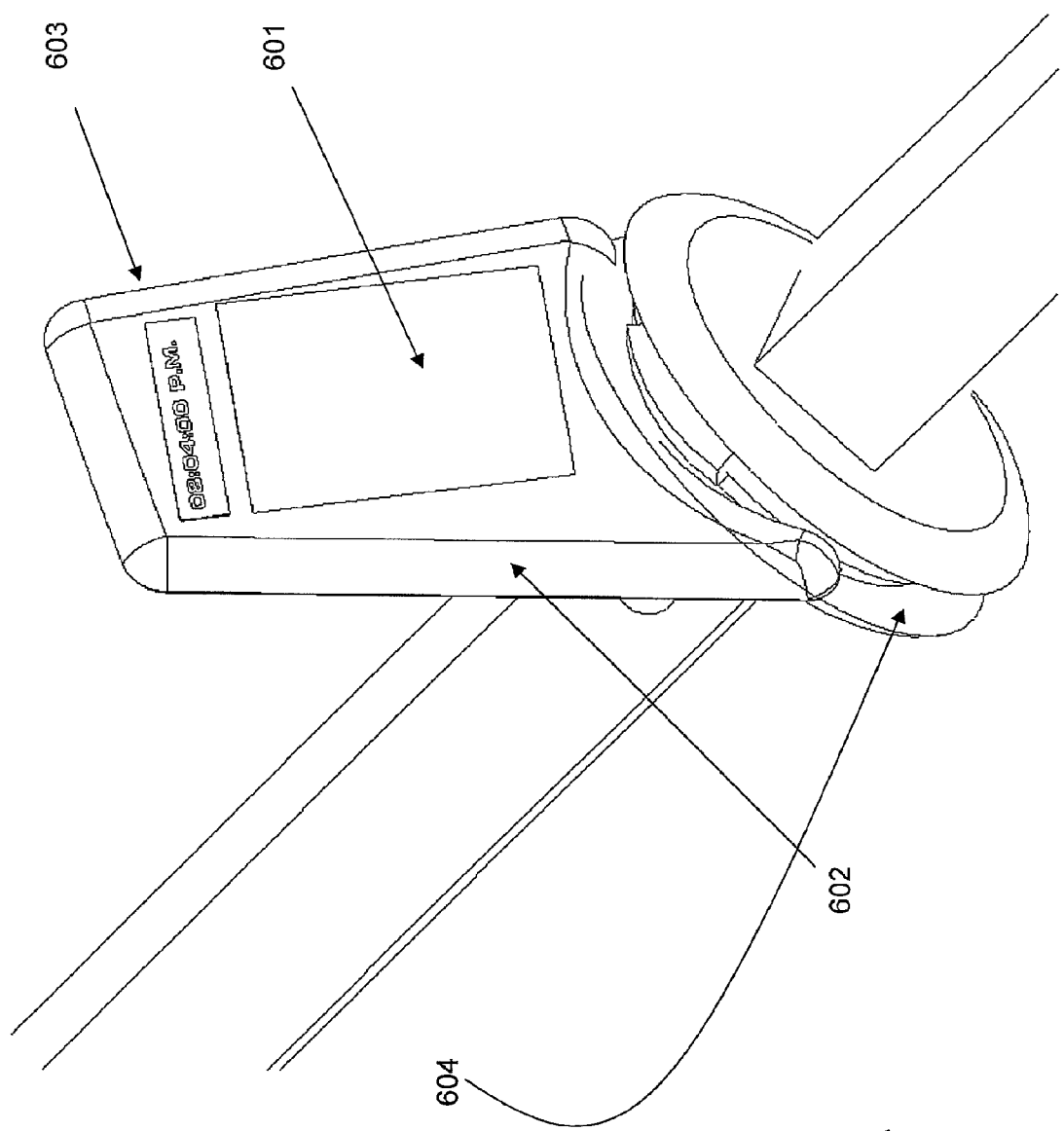
FIG. 6A illustrates the TWEEAE endoscope on-board view of video or ultrasound capture at action-end.
Figure 6B:
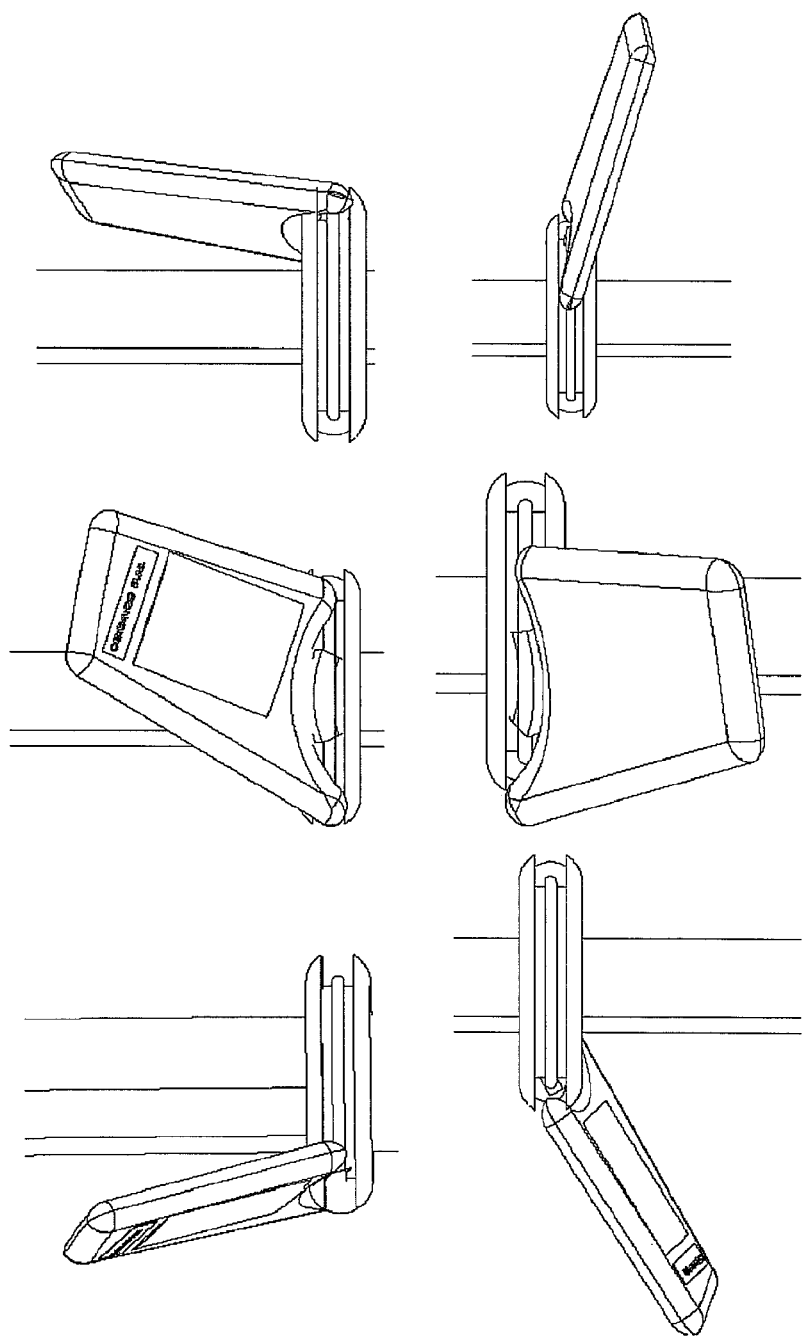
FIG. 6B illustrates examples of various positions assumable by system monitor and data display.

FIGS. 6A and 6B illustrate the endoscope on-board view of video or ultrasound capture at the action end of the endoscope. Illustrated is the monitor 601 and video processing housing 602 which can be rotated and hinged about the connecting ring 604 that can also allow automatic (gyroscopically based repositioning) or manual repositioning. The monitor 601 and video processing housing 602 consists of both monitor 601 and display which can be LCD and an alphanumeric or waveform data display 603. The processing components can include application specific or standard integrated circuits with programmable video and image processing algorithms and protocols such as image enhancement through filtering or through multiple image combinations. Data is transmitted from either CCD (charge coupled device) or CMOS (complimentary metal oxide silicon)

cameras that are fed straight to this unit (not shown) as well as to the electronic control panel 104.

FIG. 6B illustrates examples of various positioning assumable by the system monitor 601 and data display 603.

Figure 7:
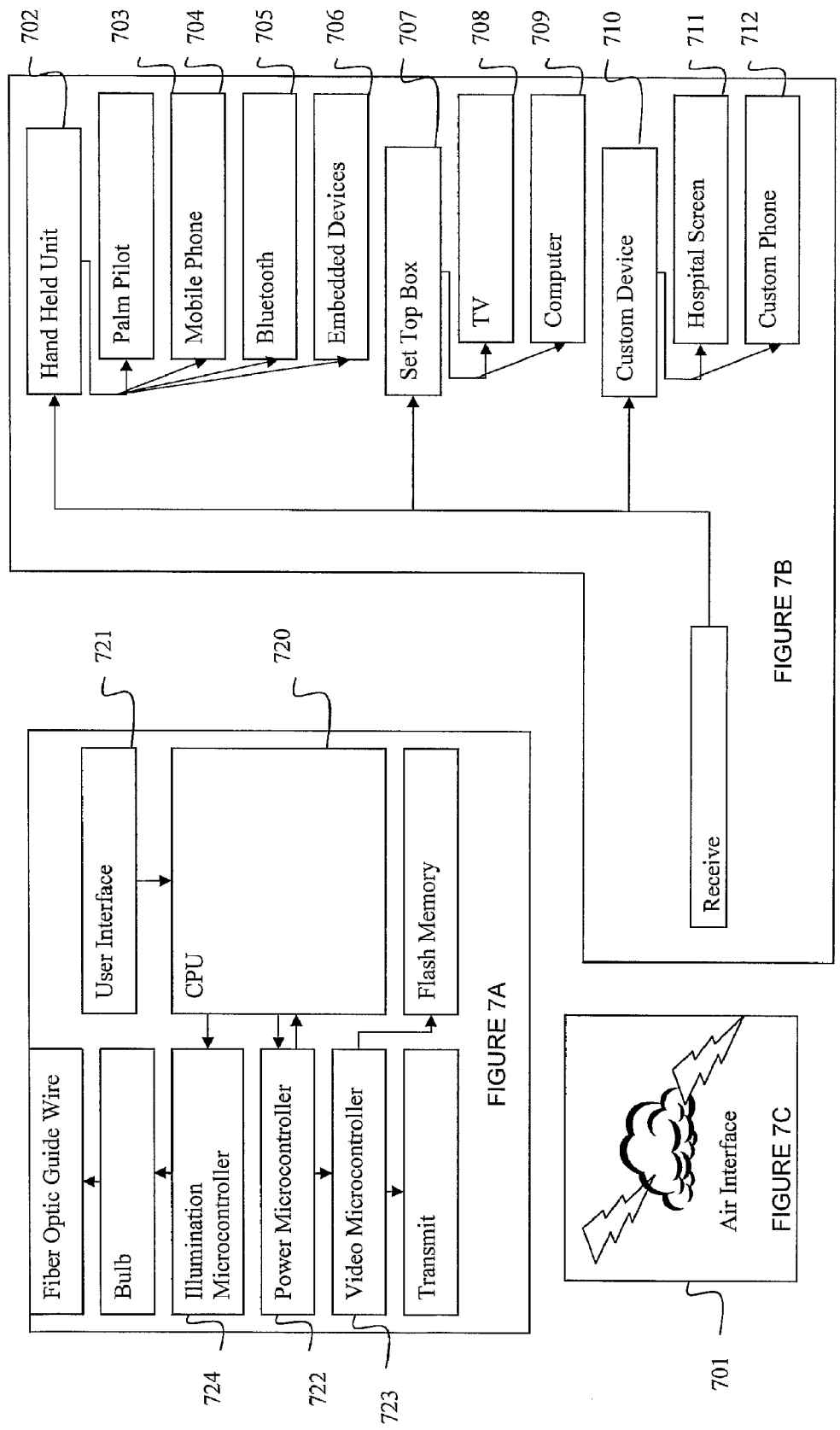
FIG. 7A illustrates the computer architecture of the TWEEAE endoscope electronics.
FIG. 7B illustrates an array of contemporary devices which can be made capable of receiving video transmissions via digital radiofrequency data packets.
FIG. 7C illustrates the air interface.

FIG. 7A represents the computer architecture of the TWEEAE electronics. FIG. 7B represents a listing of possible devices that will be made ready to receive the endoscopes transmissions. FIG. 7C illustrates a cloud and lightening icon which represents an air interface 701 of RF (radiofrequency) communication between the TWEEAE endoscope 100 and those devices listed in 7B.

In FIG. 7A the central processing unit 720 initially reacts to the user interface 721 while also interacting with the power, video and illumination micro-controllers 722-724. The power micro-controller 722 is programmed to facilitate re-charging and charge control of the battery power system. The illumination micro-controller 724 is utilized to control light intensity, mirror positioning, lasing frequencies, and reports power requirements to the CPU 720. The video microcontroller 723 interfaces with the signal processing integrated circuits as well as the transmitter and flash memory. The illumination microcontroller 723 additionally connects to the bulb which connects to the fiber optic guide wire 302.

FIG. 7B lists an array of contemporary devices which can be made capable of receiving video transmissions via digital RF data packets. These devices include hand held units 702, e.g. palm pilot 703, mobile phone 704, blue tooth enabled devices 705, embedded devices 706; set top boxes 707 that connect to televisions 708 or computers 709; and custom devices 710 e.g. a hospital screen 711, custom phone 712 and custom computers.

FIGS. 8A-E illustrate the adjustable jaw of biter at action end of endoscope.

FIG. 8A illustrates a cross-sectional orthonormal view demonstrating the mechanism of angling and positioning of the superior and inferior jaws 801, 802 to become a regular straight, up or down biter. The mechanism is initiated by rotation of pinion 803 for superior jaw position selector 804. In turn the superior jaw position selector 804 rotates the action end of superior jaw 801 about the pivot axis 805 of jaws. There is also a superior jaw gear pivot 806 and an inferior jaw pivot 807. The pinion 803 for pinion jaw position selector 804 is controlled either manually or electronically by a stepper motor (not shown). The action end of inferior jaw 802 is free in this embodiment to clamp matter against the action end of superior jaw 801. In an alternative embodiment, not illustrated, an inferior jaw position selector can be incorporated to have the inferior jaw 802 fixed and the superior jaw 801 free. Not illustrated are the fiber light guides.

Figure 8B:
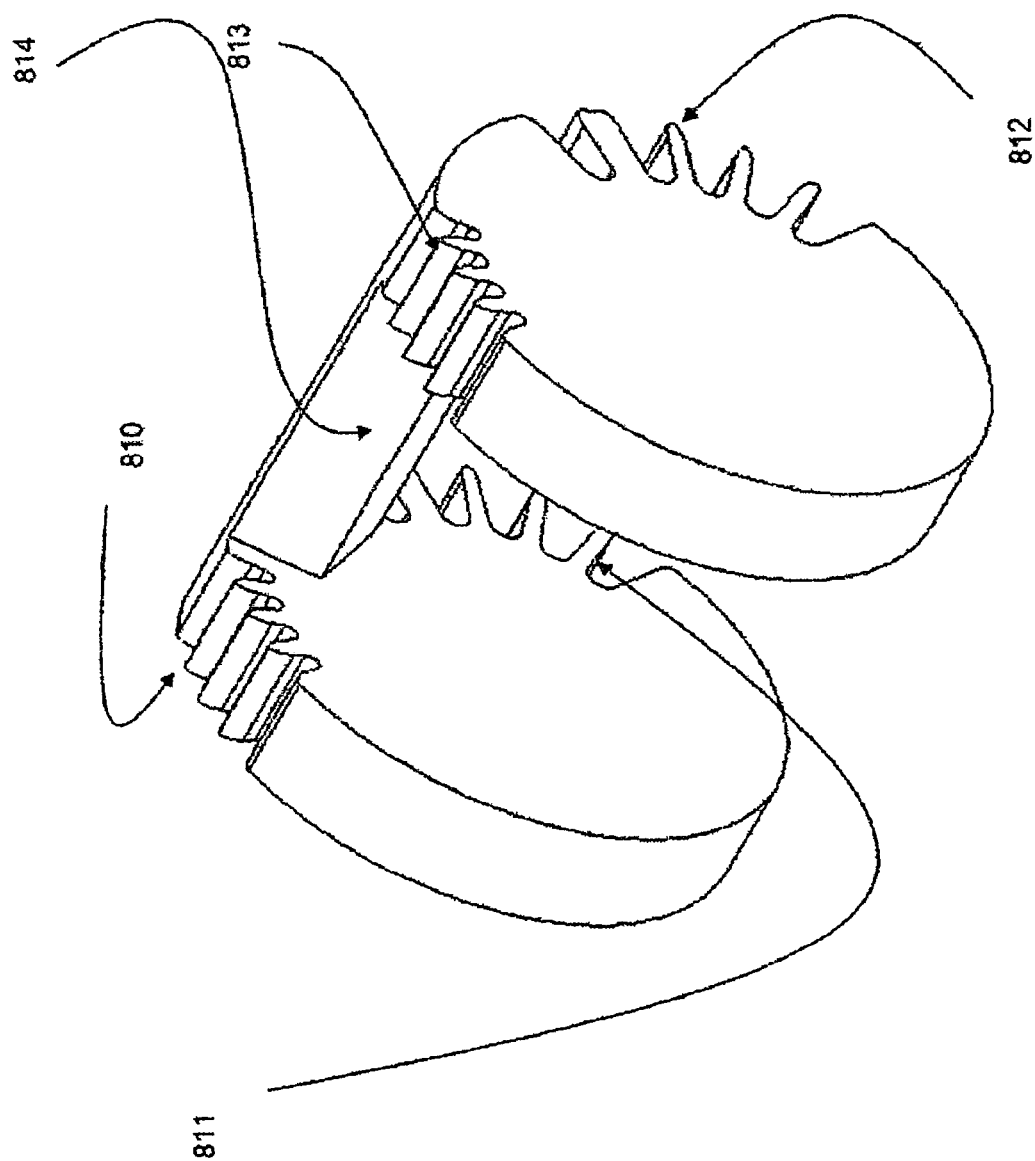
FIG. 8B illustrates a perspective view of superior jaw position selector of the TWEEAE endoscope.

FIG. 8B illustrates the perspective view of superior jaw position selector 804. Illustrated are the right pinion contact spurs 813 and left pinion contact spurs 810 which rotate the selector 804 due to the aforementioned action of the pinion 803. The right and left contacts 811, 812 with the superior jaw gear pivots serve to adjust the superior jaw angle of attack and lock it in its place. The left to right disc bridge 814 connects the left and right sides of this selector 804 while allowing free space for uncompromised passage of light fibers.

Figure 8C:
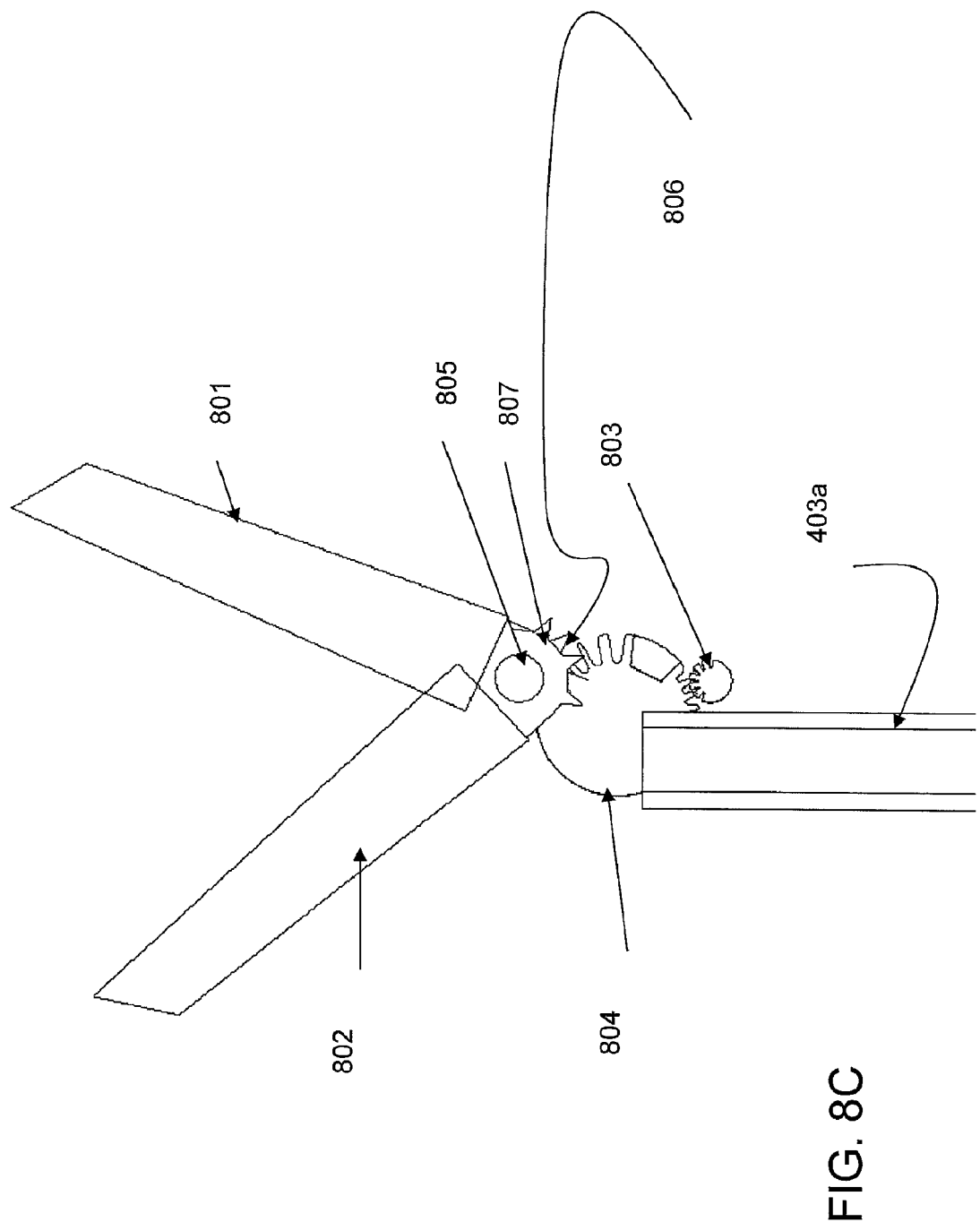
FIG. 8C illustrates a cut-away cross sectional view of the action end of the TWEEAE endoscope (inner fiber guide light present).

FIG. 8C illustrates a cut-away cross sectional view of action end of endoscope 100. This figure illustrates how the interior fibers 403a transmit laser light or radiation (preferred) or visible light through the mid-plane of the gear mesh.

Figure 8D:
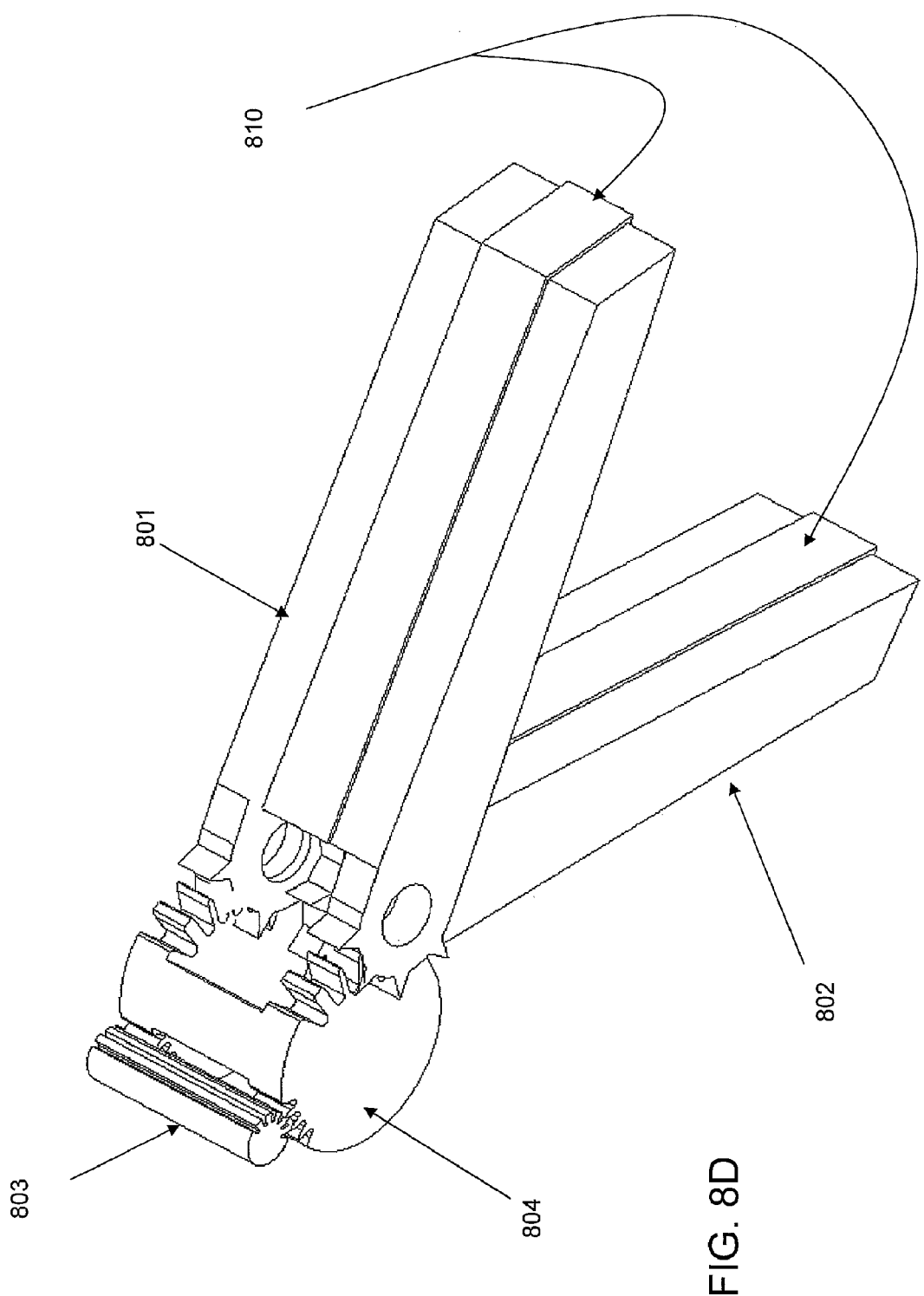
FIG. 8D illustrates a full perspective view of the TWEEAE endoscope end-manipulator with arbitrary angle superior jaw mechanism.

FIG. 8D illustrates a full perspective view of end-effector manipulator with arbitrary angle superior jaw mechanism. This illustrates a transparent midsection 810 of jaws constructed from glass or polymer. In addition it illustrates three-dimensional views of the pinion 803 for superior jaw position selector 804, the superior jaw position selector 804, and the action ends of both the inferior and superior jaws 801, 802.

Figure 8E:
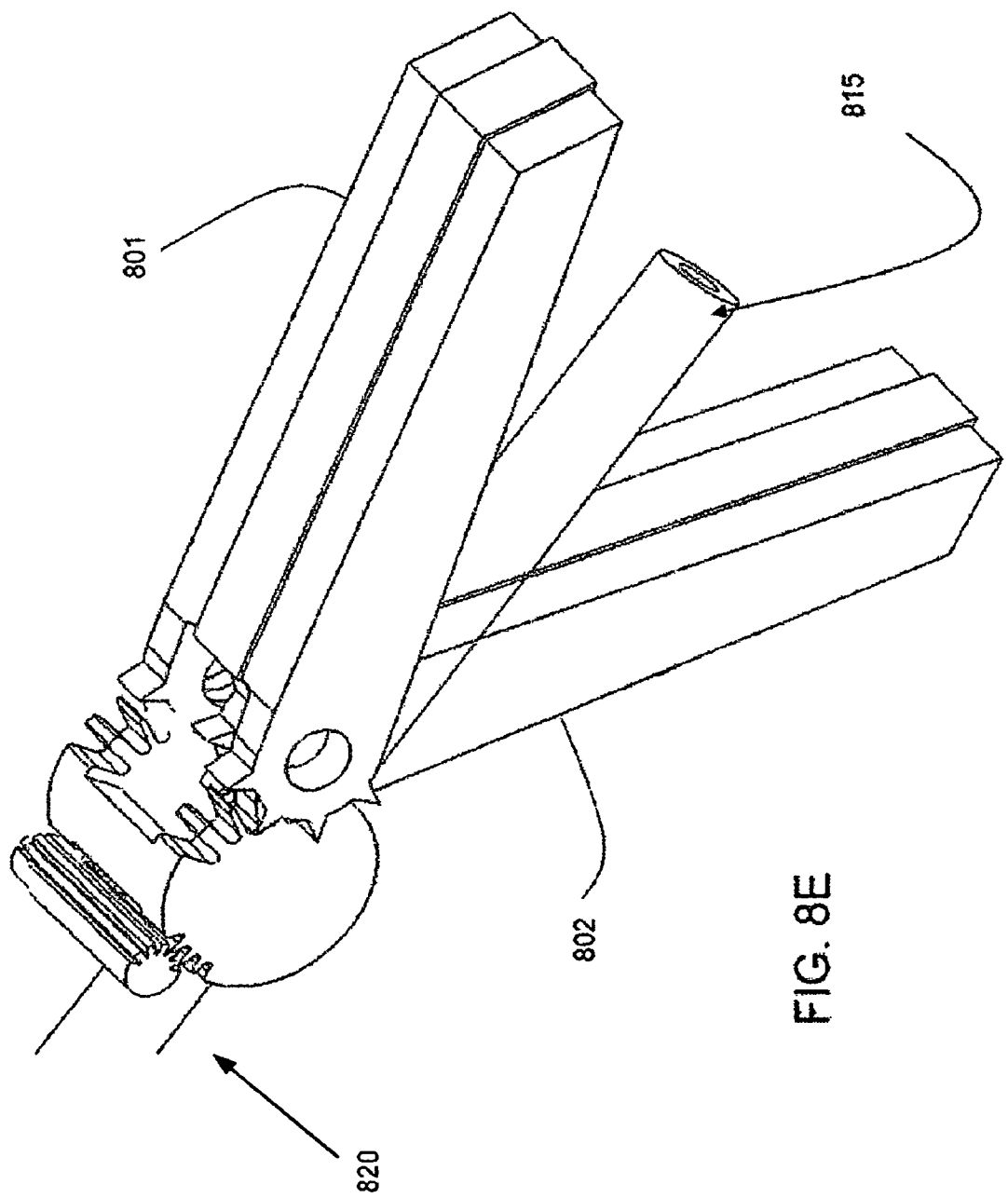
FIG. 8E illustrates the full perspective view of the TWEEAE end-effector with demonstration of laser wave front directed through midsection. Also note the area where image or video capture lenses would be positioned (lenses not drawn).

FIG. 8E in addition illustrates the imaginary expected path of laser light or radiation (preferred) or visible light (815) emanating from interior fibers 403a through end manipulator 103. Reference numeral 820 shows the area where image or video capture lenses (not shown) would be positioned in the body.

FIG. 9 illustrates the concept of rescue plates. If a standard lumbar disc plate 900A falls out, it can be replaced with a plate 900B with longer (or wider) spikes 901 or with a wider/thicker plate 900C.

Figure 10:
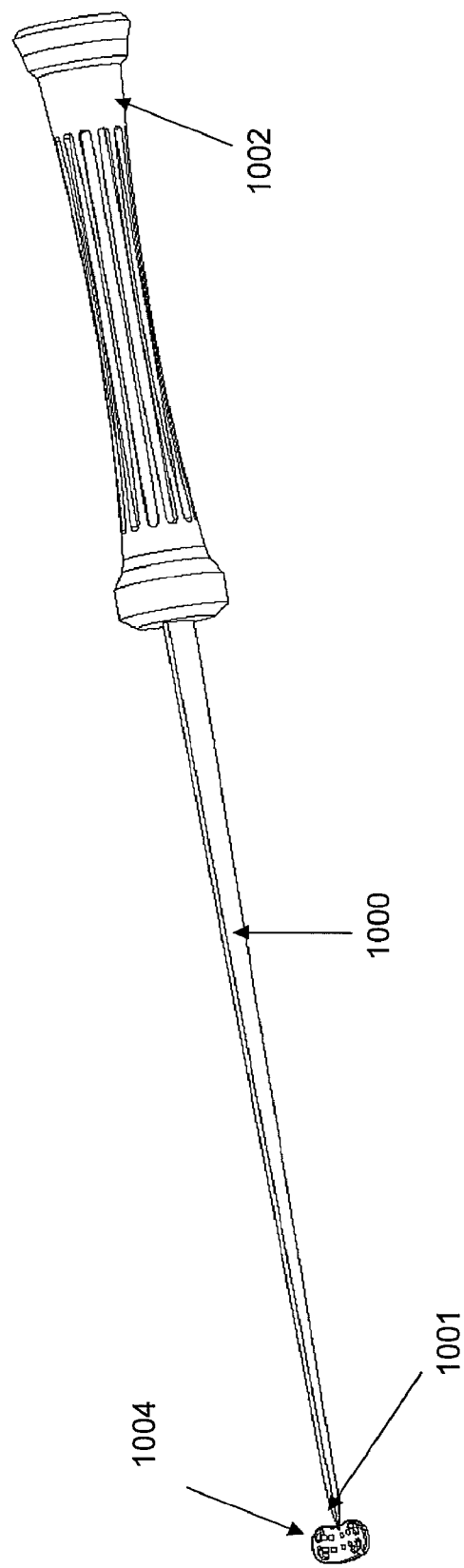
FIG. 10 illustrates a disc plate extractor.

FIG. 10 illustrates a lumbar disc plate extractor 1000. If for some reason the lumbar artificial disc 1004 must be removed in order to perform a fusion or to change plate sizes, this plate extractor 1000 can be inserted between the plate 1004 and the vertebral body. Illustrated are the sharpened end point 1001, the torque handle 1002 and the force transmitter 1003.

Figure 11A:
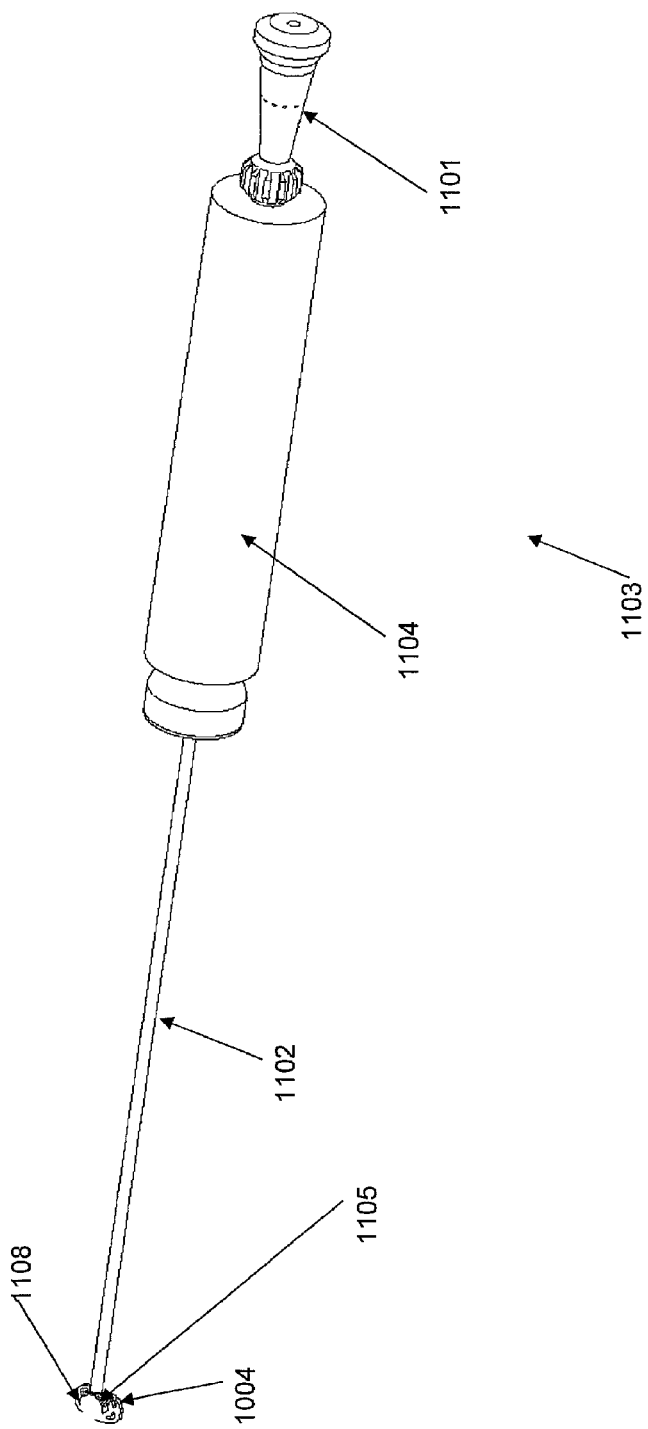
FIG. 11A illustrates an overall view of a disc ball implanter/extractor.
Figure 11B:
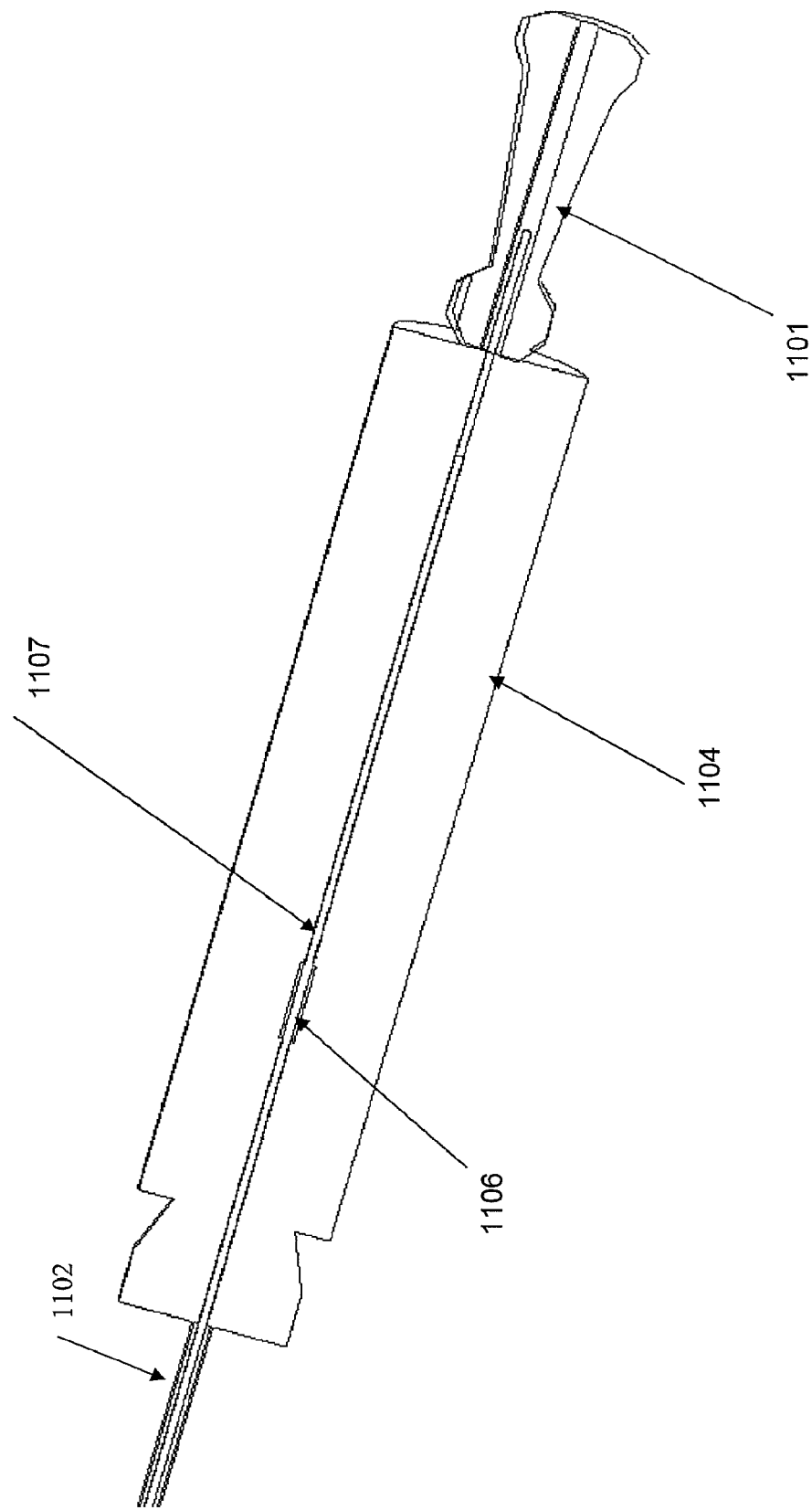
FIG. 11B illustrates a cross sectional enlargement of the disc ball extractor handle.

FIGS. 11A and 11B illustrate a disc ball implanter/explantor 1100. The instrument 1100 is composed of a tightening knob 1101 which rotates a pinion shaft key 1106 attached to a pinion shaft 1107 which then opens and closes, i.e. releases or grabs the disc ball 1108 with enclosing semi circles grapplers 1105. A pinion shaft enclosure 1102 encloses pinion shaft 1107. FIG. 11B is an enlargement cross sectional view of the disc ball extractor handle 1103.

Figure 11C:
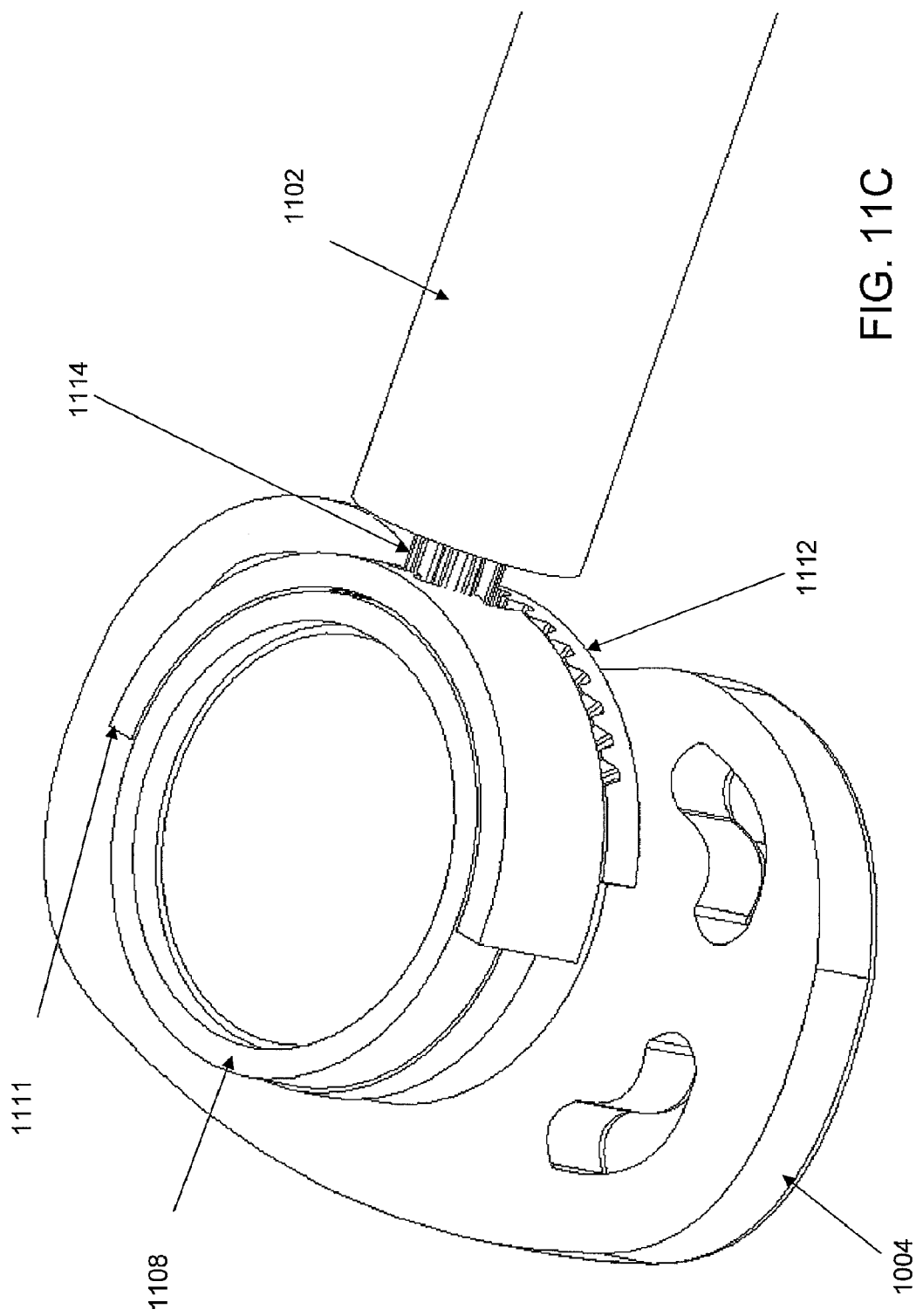
FIG. 11C illustrates an enlargement of the disc ball extractor grappler.

FIG. 11C is an enlargement of the disc ball extractor grappler 1105. This demonstrates the interface of the left enclosing semicircle 1111 and right enclosing semi-circle 1112 with the disc ball 1108. Also demonstrated is the pinion 1114, as well as the disc plate 1004 in the background.

Figure 11D:
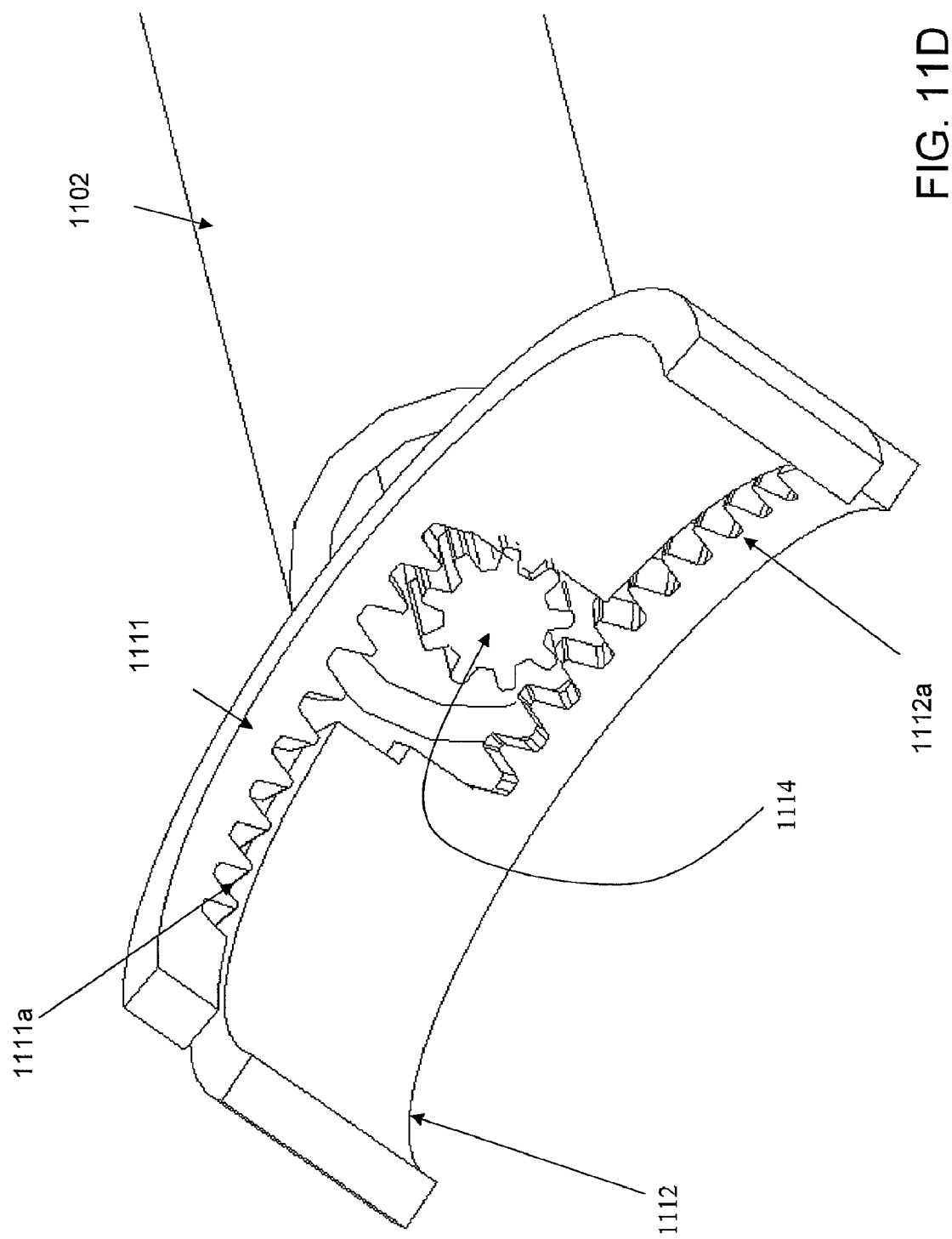
FIG. 11D illustrates an enlarged view of the grappler in opened position.

FIG. 11D illustrates the grappler 1105 in an opened position. Centrally illustrated is the pinion 1114 inter-digitating with the left semi-circle spur rack 1112a and the right semi-circle spur rack 1111a.

Figure 11E:
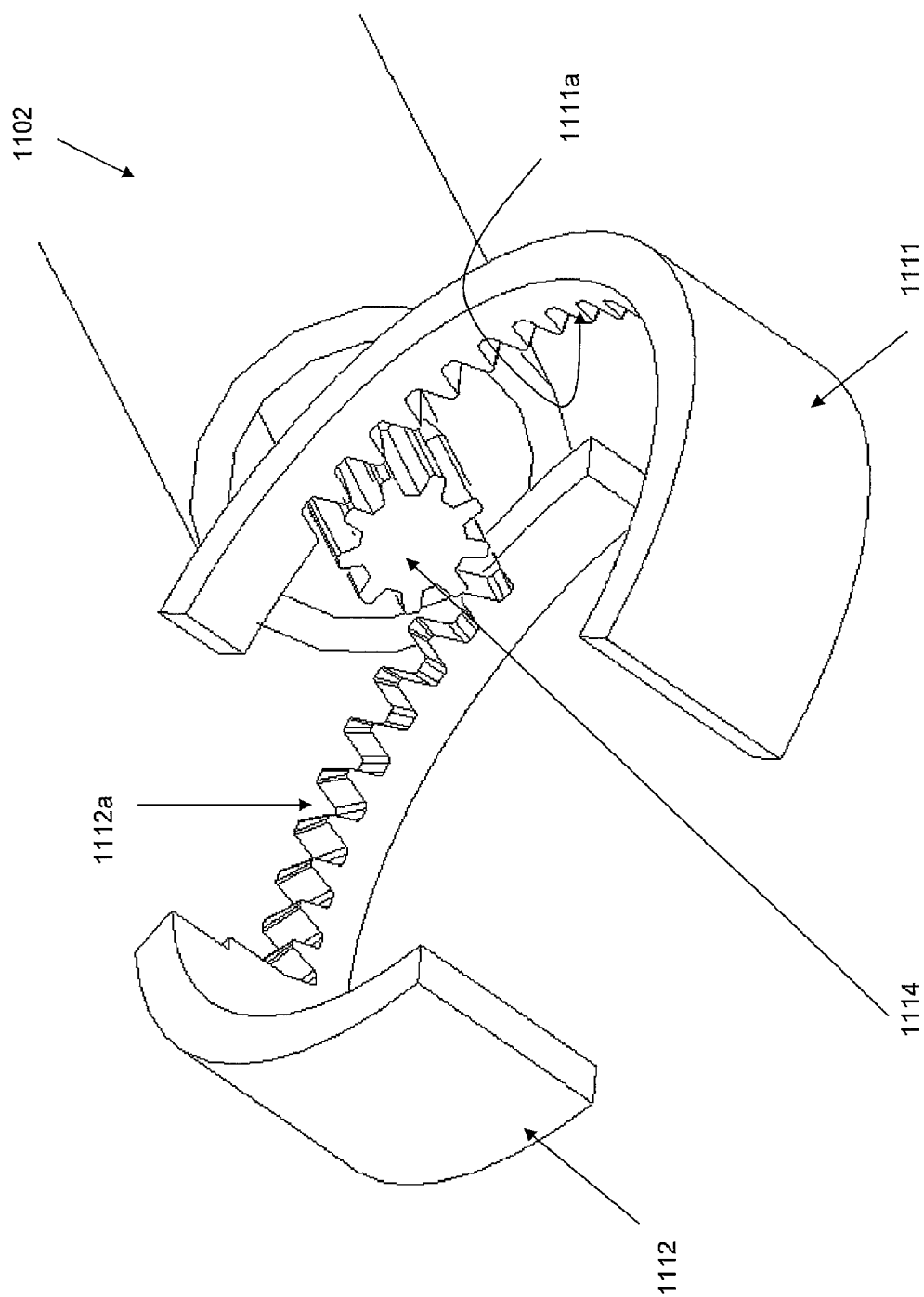
FIG. 11E illustrates the grappler in closed position.

FIG. 11E illustrates the grappler 1105 in closed position. Note how the semicircles 1111, 1112 have moved away from each other by reversing inter-digitating directions along the pinion 1114.

Figure 11F:
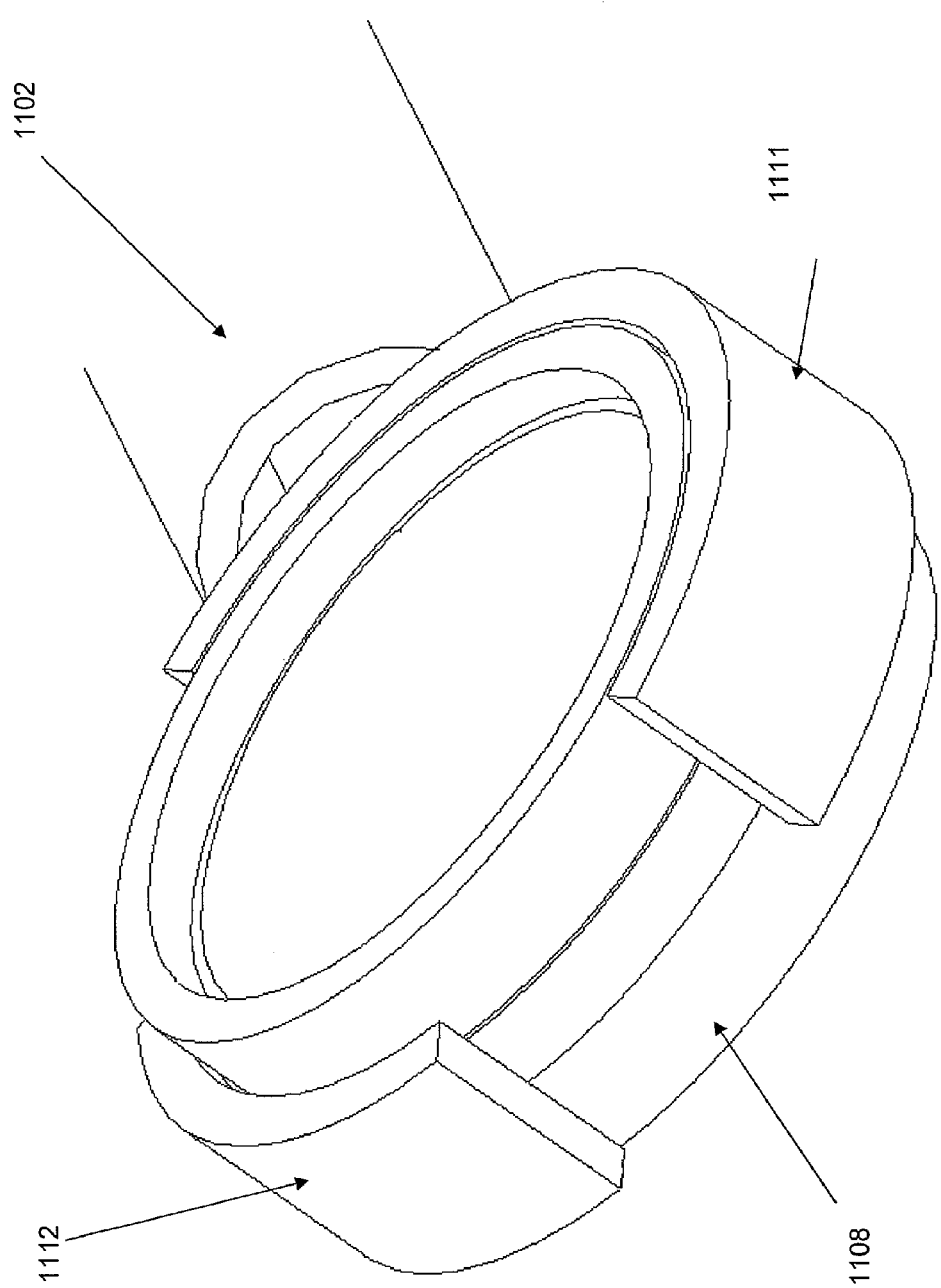
FIG. 11F illustrates the grappler in closed position with disc ball.

FIG. 11F illustrates the same image of 9E with a ball 1108 inside, demonstrating how it is grasped.

The inventions described herein further enhance the capacity to implant and explant posteriorly placed artificial discs. The unique totally wireless electronically embedded action ended endoscope herein described has the capacity to revolutionize and simplify the current practice of endoscopy in lumbar spinal surgery as well as all spheres of surgical and medical subspecialties utilizing endoscopy. It is also uniquely adapted for the military surgical field, and emergency, ambulatory and aerospace medical technology.

We claim:

1. A hand manipulated endoscopic medical device, comprising:
    a tool body having a proximal end and a distal end;
    a pair of hand-operated manipulators at the proximal end;
        a pair of forceps at the distal end, the pair of forceps responsive to operation of the pair of hand-operated manipulators, wherein each of the pair of forceps is rotatable about an axis, and wherein an angle of attack of each of the pair of forceps is adjustable, and wherein each of the pair of forceps includes a jaw pivot gear;
a pinion controlled one of manually and electronically;
a position selector engaging each of the pair of forceps and the pinion, wherein rotation of the pinion moves the position selector, which rotates at least one of the pair of forceps about the axis;
a light emitting device having a light generator disposed in the tool body at the proximal end of the tool body, the light emitting device configured to emit light, which is generated by the light generator, at the pair of forceps, the light emitting device disposed in the tool body; and
an imaging device configured to capture images at the pair of forceps, the imaging device disposed in the tool body,
wherein the position selector comprises:
a first side having a plurality of first pinion contact spurs and a second side having a plurality of second pinion contact spurs, the first and second pinion contact spurs arranged to engage the pinion, wherein rotation of the pinion acts on the first and second pinion contact spurs to rotate the position selector; and
a plurality of first contacts engaging the jaw pivot gear of a first one of the pair of forceps and a plurality of second contacts engaging the jaw pivot gear of a second one of the pair of forceps, wherein rotation of the position selector adjusts the angle of attack of each of the pair of forceps and locks the angle of attack in place.

2. The medical device of claim 1, wherein the position selector comprises:
a bridge connecting the left and right sides of the position selector while allowing free space for passage of the light emitting device.

3. The medical device of claim 1, further including an electronics unit that controls the light emitting device and the imaging device.

4. The medical device of claim 3, further including a device for transferring data or video from the endoscopic medical device.

5. The medical device of claim 4, further including at least a data transfer device selected from the group consisting of a wireless connection, a wired connection, an optical connection, and a removable memory device.

6. The medical device of claim 3, further including a receiver responsive to the electronics unit, wherein the receiver is capable of communicating with at least one of a handheld unit, a Palm Pilot, a mobile phone, a Bluetooth device, an embedded device, a set top box, a TV, a computer, a custom device, a hospital screen, and a custom phone.

7. The medical device of claim 1, further including a battery compartment for a battery that provides power for the light emitting device and the imaging device.

8. The medical device of claim 1, further including a display disposed on the tool body, and
wherein the display is positionable relative to the tool body of the medical device.

9. The medical device of claim 8, wherein the display includes a connecting ring for adjusting the display.

10. The medical device of claim 8, wherein the display is a gyroscopically adjustable display.

11. The medical device of claim 1, wherein an angle of attack of the pair of hand-operated manipulators is adjustable.

12. The medical device of claim 1, wherein the light emitting device includes one of a laser, a LED, and a bulb.

13. The medical device of claim 1, further including a spark voltage generator and magneto circuitry.

14. The medical device of claim 1, further including one of a plurality of interior optical fibers for transmitting light including visible light or laser radiation, and
a plurality of exterior optical fibers for transmitting light including visible light or laser radiation.

15. The medical device of claim 14, wherein at least some of the exterior optical fibers or interior optical fibers terminate at one of:
elliptical semi-enclosed directive reflectors, which can be electronically or mechanically positioned, and
at least one of Risley prisms and semi-coated mirrors that can be electronically positioned.

16. The medical device of claim 14, wherein at least some of the exterior optical fibers or interior optical fibers terminate at a beam steering element configured to be at one of electronically positioned and mechanically positioned.

17. The medical device of claim 1, further including a fiber optic wave guide.

18. The medical device of claim 1, wherein the medical device further includes a wireless interface for communicating data to a receiver.

19. The medical device of claim 1, wherein each of the pair of forceps includes a transparent midsection.

* * * * *